(12) United States Patent
Cizeau et al.

(10) Patent No.: US 8,263,744 B2
(45) Date of Patent: Sep. 11, 2012

(54) BINDING PROTEINS THAT BIND TO EPCAM LINKED TO AN EFFECTOR MOLECULE

(75) Inventors: Jeannick Cizeau, Winnipeg (CA); Glen Christopher Macdonald, Winnipeg (CA)

(73) Assignee: Viventia Biotechnologies Inc., Mississauga, Ontario (CA)

( * ) Notice: Subject to any disclaimer, the term of this patent is extended or adjusted under 35 U.S.C. 154(b) by 291 days.

(21) Appl. No.: 12/596,188

(22) PCT Filed: Apr. 18, 2008

(86) PCT No.: PCT/CA2008/000711
§ 371 (c)(1),
(2), (4) Date: Feb. 8, 2010

(87) PCT Pub. No.: WO2008/128330
PCT Pub. Date: Oct. 30, 2008

(65) Prior Publication Data
US 2010/0145023 A1    Jun. 10, 2010

Related U.S. Application Data

(60) Provisional application No. 60/912,732, filed on Apr. 19, 2007.

(51) Int. Cl.
*C07K 16/00*    (2006.01)
*C07K 17/00*    (2006.01)
*C07K 17/14*    (2006.01)
*C12P 21/08*    (2006.01)
*A61K 39/395*   (2006.01)
*A61K 39/00*    (2006.01)

(52) U.S. Cl. ............... 530/387.1; 530/391.1; 530/391.7; 424/130.1; 424/178.1; 424/183.1

(58) Field of Classification Search ................. None
See application file for complete search history.

(56) References Cited

U.S. PATENT DOCUMENTS

| | | | |
|---|---|---|---|
| 5,082,767 | A | 1/1992 | Hatfield et al. |
| 6,339,070 | B1 | 1/2002 | Emery et al. |
| 7,655,437 | B2 | 2/2010 | Jevsevar et al. |
| 2003/0148950 | A1 | 8/2003 | Xin et al. |
| 2007/0196366 | A1 | 8/2007 | Zangemeister-Wittke et al. |

FOREIGN PATENT DOCUMENTS

| WO | WO 98/55623 | 12/1998 |
|---|---|---|
| WO | WO 9965521 A1 | 12/1999 |
| WO | WO 2004096271 A1 | 11/2004 |
| WO | WO 2005/090579 | 9/2005 |
| WO | WO 2005/121341 | 12/2005 |

OTHER PUBLICATIONS

Gherardi et al., Structural basis of haptocyte growth factor/scatter factor and MET signalling, Proc. Nat. Acad. Sci. USA, 103(11):4046-4051, Mar. 14, 2006.

*Primary Examiner* — Anne M. Gussow
(74) *Attorney, Agent, or Firm* — Bereskin & Parr LLP/S.E.N.C.R.L., s.r.l.; Micheline Gravelle

(57) ABSTRACT

An optimized nucleic acid sequence encoding the immunoconjugate VB6-845 is described Modifications to the original VB6-845 include changes in the nucleic acid sequence encoding the $V_H$ region, $C_H$ region, $C_L$ region, $V_L$ region, the furm linker and the bouganm toxin. The optimized VB6-845 displays improved recombinant protein expression over the original in an *E. coli* expression system.

8 Claims, 14 Drawing Sheets

FIGURE 1

Original VB6-845 Nucleotide and Amino Acid Sequence (SEQ ID 1 and 2)

```
GAA TTC CTG CAG GTC TAT GGA ACG ATA AAT GCC CAT GAA AAT TCT ATT TCA AGG
                                                                    RBS site AGA CAG TCA TA ATG AAA TAC CTA TTG CCT ACG GCA GCC GCT GGA TTG TTA TTA
               M   K   Y   L   L   P   T   A   A   A   G   L   L   L
               [_____ PelB Leader Sequence CTC GCT GCC CAA CCA GCG ATG GCG CAC CAT CAT CAC CAT CAC GAA GTA CAG CTG
 L   A   A   Q   P   A   M   A   H   H   H   H   H   H   E   V   Q   L
_____]         6xHis            [-----V_H Start GTT CAG TCC GGC CCG GGT CTT GTT CAA CCG GGT GGT TCC GTT CGT ATC TCT TGC
 V   Q   S   G   P   G   L   V   Q   P   G   G   S   V   R   I   S   C GCT GCT TCT GGT TAC ACG TTC ACC AAC TAC GGC ATG AAC TGG GTC AAA CAG GCT
 A   A   S   G   Y   T   F   T   N   Y   G   M   N   W   V   K   Q   A
                                 |———— CDR 1 ————|

CCG GGT AAA GGC CTG GAA TGG ATG GGC TGG ATC AAC ACC TAC ACC GGT GAA TCC
 P   G   K   G   L   E   W   M   G   W   I   N   T   Y   T   G   E   S
                                     |—————————————————— CDR 2——————

ACC TAC GCT GAC TCC TTC AAA GGT CGC TTC ACT TTC TCC CTC GAC ACA AGT GCT
 T   Y   A   D   S   F   K   G   R   F   T   F   S   L   D   T   S   A
——————————————————————————————|

AGT GCT GCA TAC CTC CAA ATC AAC TCG CTG CGT GCA GAG GAT ACA GCA GTC TAT
 S   A   A   Y   L   Q   I   N   S   L   R   A   E   D   T   A   V   Y

TAC TGC GCC CGT TTC GCT ATC AAA GGT GAC TAC TGG GGT CAA GGC ACG CTG CTG
 Y   C   A   R   F   A   I   K   G   D   Y   W   G   Q   G   T   L   L
                 |————CDR3————|

ACC GTT TCC TCG GCT AGC ACC AAA GGC CCA TCG GTC TTC CCC CTG GCA CCC TCC
 T   V   S   S   A   S   T   K   G   P   S   V   F   P   L   A   P   S
V_H End --------||------------ C_H Start TCC AAG AGC ACC TCT GGG GGC ACA GCG GCC CTG GGC TGC CTG GTC AAG GAC TAC
 S   K   S   T   S   G   G   T   A   A   L   G   C   L   V   K   D   Y TTC CCC GAA CCG GTG ACG GTG TCG TGG AAC TCA GGC GCC CTG ACC AGC GGC GTG
 F   P   E   P   V   T   V   S   W   N   S   G   A   L   T   S   G   V CAC ACC TTC CCG GCT GTC CTA CAG TCC TCA GGA CTC TAC TCC CTC AGC AGC GTG
 H   T   F   P   A   V   L   Q   S   S   G   L   Y   S   L   S   S   V GTG ACC GTG CCC TCC AGC AGC TTG GGC ACC CAG ACC TAC ATC TGC AAC GTG AAT
 V   T   V   P   S   S   S   L   G   T   Q   T   Y   I   C   N   V   N

CAC AAG CCC AGC AAC ACC AAG GTG GAC AAG AAA GTT GAG CCC AAA TCT TGT TAG
```

FIGURE 1 (cont'd)

```
            H   K   P   S   N   T   K   V   D   K   K   V   E   P   K   S   C
                                                                    V_H end -------|
TGA TCT AGA GTC GAC CTG CAG GTC TAT GGA ACG ATA AAT GCC CAT GAA AAT TCT ATT TCA AGG AGA CAG TCA TA  ATG AAA TAC CTA TTG CCT ACG GCA GCC GCT GGA
                             M   K   Y   L   L   P   T   A   A   A   G
                            |_____PelB Leader Sequence_____

TTG TTA TTA CTC GCT GCC CAA CCA GCG ATG GCG GAT ATC CAG ATG ACC CAG TCC
 L   L   L   L   A   A   Q   P   A   M   A   D   I   Q   M   T   Q   S
_____||----------- V_L Start CCG TCC TCC CTG AGT GCT TCT GTT GGT GAC CGT GTT ACC ATC ACC TGC CGT TCC
 P   S   S   L   S   A   S   V   G   D   R   V   T   I   T   C   R   S
                                                                 |----

ACC AAA TCC CTC CTG CAC TCC AAC GGT ATC ACC TAC CTT TAT TGG TAT CAA CAG
 T   K   S   L   L   H   S   N   G   I   T   Y   L   Y   W   Y   Q   Q
-----------------------CDR 1----------------------|

AAA CCG GGT AAA GCT CCG AAA CTT CTG ATC TAC CAG ATG TCC AAC CTG GCT TCC
 K   P   G   K   A   P   K   L   L   I   Y   Q   M   S   N   L   A   S
                                         |------ CDR 2 ------|

GGT GTT CCG TCT CGT TTC TCC AGT TCT GGT TCT GGT ACC GAC TTC ACC CTG ACC
 G   V   P   S   R   F   S   S   S   G   S   G   T   D   F   T   L   T

ATC TCT TCT CTG CAG CCG GAA GAC TTC GCT ACC TAC TAC TGC GCT CAG AAC CTG
 I   S   S   L   Q   P   E   D   F   A   T   Y   Y   C   A   Q   N   L
                                                        |--------CDR 3

GAA ATC CCG CGT ACC TTC GGT CAG GGT ACC AAA GTT GAA CTT AAG CGC ACT GTG
 E   I   P   R   T   F   G   Q   G   T   K   V   E   L   K   R   T   V
---------------|                                    V_L End ---||C_L Start GCT GCA CCA TCT GTC TTC ATC TTC CCG CCA TCT GAT GAG CAG TTG AAA TCT GGA
 A   A   P   S   V   F   I   F   P   P   S   D   E   Q   L   K   S   G ACT GCC TCT GTT GTG TGC CTG CTG AAT AAC TTC TAT CCC AGA GAG GCC AAA GTA
 T   A   S   V   V   C   L   L   N   N   F   Y   P   R   E   A   K   V CAG TGG AAG GTG GAT AAC GCC CTC CAA TCG GGT AAC TCC CAG GAG AGT GTC ACA
 Q   W   K   V   D   N   A   L   Q   S   G   N   S   Q   E   S   V   T GAG CAG GAC AGC AAG GAC AGC ACC TAC AGC CTC AGC AGC ACC CTG ACG CTG AGC
 E   Q   D   S   K   D   S   T   Y   S   L   S   S   T   L   T   L   S AAA GCA GAC TAC GAG AAA CAC AAA GTC TAC GCC TGC GAA GTC ACC CAT CAG GGC
 K   A   D   Y   E   K   H   K   V   Y   A   C   E   V   T   H   Q   G CTG AGC TCG CCC GTC ACA AAG AGC TTC AAC AGG GGA GAG TGT ACC AGG CAC AGG
 L   S   S   P   V   T   K   S   F   N   R   G   E   C   T   R   H   R
                                        C_L End -------||---- Furin
```

FIGURE 1 (cont'd)

```
CAG CCC AGA GGC TGG GAG CAG CTC TAC AAC ACC GTG TCA TTT AAC CTT GGA GAA
 Q   P   R   G   W   E   Q   L   Y   N   T   V   S   F   N   L   G   E
linker ---------------------|  |------- de-bouganin Start GCT TAT GAG TAC CCC ACT TTT ATA CAA GAT TTG CGC AAT GAA TTG GCT AAG GGC
 A   Y   E   Y   P   T   F   I   Q   D   L   R   N   E   L   A   K   G ACA CCA GTA TGT CAA CTT CCA GTG ACA CTA CAA ACC ATA GCC GAT GAC AAG CGA
 T   P   V   C   Q   L   P   V   T   L   Q   T   I   A   D   D   K   R TTT GTT CTA GTT GAT ATC ACT ACG ACC TCG AAG AAA ACA GTT AAG GTT GCT ATA
 F   V   L   V   D   I   T   T   T   S   K   K   T   V   K   V   A   I GAT GTG ACA GAT GTG TAT GTT GTG GGT TAT CAA GAC AAA TGG GAT GGC AAA GAT
 D   V   T   D   V   Y   V   V   G   Y   Q   D   K   W   D   G   K   D CGA GCT GTT TTC CTT GAC AAG GTT CCT ACT GTT GCA ACT AGT AAA CTT TTC CCA
 R   A   V   F   L   D   K   V   P   T   V   A   T   S   K   L   F   P GGG GTG ACT AAT CGT GTA ACG TTA ACA TTT GAT GGC AGC TAT CAG AAA CTT GTG
 G   V   T   N   R   V   T   L   T   F   D   G   S   Y   Q   K   L   V AAT GCT GCC AAA GCT GAT AGA AAG GCT CTC GAA CTG GGG GTT AAC AAA TTG GAA
 N   A   A   K   A   D   R   K   A   L   E   L   G   V   N   K   L   E TTT TCC ATT GAA GCA ATC CAT GGT AAA ACG ATA AAT GGT CAA GAG GCA GCC AAG
 F   S   I   E   A   I   H   G   K   T   I   N   G   Q   E   A   A   K TTC TTT CTT ATT GTC ATC CAA ATG GTT TCA GAG GCA GCT CGG TTC AAA TAT ATT
 F   F   L   I   V   I   Q   M   V   S   E   A   A   R   F   K   Y   I GAG ACT GAG GTG GTT GAT AGA GGA TTA TAT GGA TCA TTC AAA CCT AAT TTT AAA
 E   T   E   V   V   D   R   G   L   Y   G   S   F   K   P   N   F   K GTA TTG AAC TTG GAG AAC AAT TGG GGC GAC ATC TCT GAT GCC ATT CAC AAA TCA
 V   L   N   L   E   N   N   W   G   D   I   S   D   A   I   H   K   S TCC CCA CAA TGT ACC ACT ATT AAT CCG GCA CTT CAG TTG ATA AGC CCC TCA AAT
 S   P   Q   C   T   T   I   N   P   A   L   Q   L   I   S   P   S   N GAC CCA TGG GTT GTA AAT AAA GTG AGT CAA ATT AGT CCC GAT ATG GGT ATC CTT
 D   P   W   V   V   N   K   V   S   Q   I   S   P   D   M   G   I   L AAG TTT AAA AGC TCC AAA TAG TGA CTC GAG
 K   F   K   S   S   K
                       de-bouganin End -------|
```

FIGURE 2

Optimized VB6-845 Nucleotide and Amino Acid Sequence with New RBS (SEQ ID 3 and 4)

```
AAGGA GAA TTC CATA ATG AAA TAT CTG CTG CCG ACT GCT GCT GCG GGT CTG CTG CTG
New RBS              M   K   Y   L   L   P   T   A   A   A   G   L   L   L
               |_____ PelB Leader Sequence _____

CTG GCT GCG CAA CCG GCT ATG GCT CAT CAC CAC CAC CAC CAT GAG GTT CAG CTG
 L   A   A   Q   P   A   M   A   H   H   H   H   H   H   E   V   Q   L
_____|        6xHis         |------Vн Start GTC CAG TCC GGT CCG GGT CTG GTT CAG CCG GGT GGT AGC GTT CGT ATT AGC TGC
 V   Q   S   G   P   G   L   V   Q   P   G   G   S   V   R   I   S   C GCG GCG AGC GGT TAC ACC TTC ACC AAC TAC GGT ATG AAC TGG GTT AAA CAG GCT
 A   A   S   G   Y   T   F   T   N   Y   G   M   N   W   V   K   Q   A
                                  |—— CDR 1 ——|

CCG GGT AAA GGT TTG GAA TGG ATG GGT TGG ATC AAC ACC TAT ACC GGT GAG TCT
 P   G   K   G   L   E   W   M   G   W   I   N   T   Y   T   G   E   S
                                   |————————— CDR 2 —————————

ACC TAC GCT GAT AGC TTC AAA GGC CGT TTC ACC TTT AGC CTT GAC ACT TCT GCG
 T   Y   A   D   S   F   K   G | R   F   T   F   S   L   D   T   S   A

AGC GCG GCG TAC CTG CAG ATT AAC TCT CTG CGT GCT GAG GAC ACT GCG GTT TAC
 S   A   A   Y   L   Q   I   N   S   L   R   A   E   D   T   A   V   Y

TAC TGC GCT CGT TTC GCG ATC AAA GGT GAC TAT TGG GGT CAG GGT ACT CTG CTG
 Y   C   A   R   F   A   I   K   G   D   Y   W   G   Q   G   T   L   L
                   |——————— CDR3 ———————|

ACC GTT AGC AGC GCT AGC ACT AAA GGT CCG TCC GTT TTC CCA CTG GCT CCG TCT
 T   V   S   S   A   S   T   K   G   P   S   V   F   P   L   A   P   S
Vн End --------||-------- Cн Start TCT AAA AGC ACT TCT GGT GGT ACC GCG GCT CTG GGT TGC CTT GTT AAA GAC TAC
 S   K   S   T   S   G   G   T   A   A   L   G   C   L   V   K   D   Y TTC CCT GAA CCG GTC ACC GTT AGC TGG AAC TCC GGT GCG TTG ACC TCT GGT GTT
 F   P   E   P   V   T   V   S   W   N   S   G   A   L   T   S   G   V CAC ACC TTC CCA GCG GTT CTG CAG TCT AGC GGT CTG TAT AGC CTG AGC TCT GTA
 H   T   F   P   A   V   L   Q   S   S   G   L   Y   S   L   S   S   V GTT ACC GTT CCG TCT TCT AGC CTG GGT ACG CAG ACC TAC ATC TGC AAC GTG AAC
 V   T   V   P   S   S   S   L   G   T   Q   T   Y   I   C   N   V   N
```

FIGURE 2 (cont'd)

```
CAC AAA CCG AGC AAC ACT AAA GTG GAT AAA AAA GTT GAA CCG AAG TCT TGC TAG
 H   K   P   S   N   T   K   V   D   K   K   V   E   P   K   S   C
                                                                    C_H
TGA TCT AGA GTC GAC CTG CAG GTC TAT GGA ACG ATA AAT GCC CAT GAA AAT TCT
end-|

ATT TCA AGG AGA CAG TCA TA ATG AAA TAC CTT CTG CCG ACC GCT GCC GCT GGT
                            M   K   Y   L   L   P   T   A   A   A   G
                           |_____PelB Leader Sequence CTG CTG CTG TTG GCT GCT CAA CCG GCT ATG GCA GAC ATC CAG ATG ACC CAG TCC
 L   L   L   L   A   A   Q   P   A   M   A   D   I   Q   M   T   Q   S
_____|  |----------- V_L Start CCG TCT AGC CTG AGC GCA AGC GTT GGT GAC CGT GTG ACC ATC ACC TGC CGT AGC
 P   S   S   L   S   A   S   V   G   D   R   V   T   I   T   C  |R   S ACT AAA TCC CTG CTG CAC TCT AAC GGC ATC ACC TAC CTG TAT TGG TAC CAA CAG
 T   K   S   L   L   H   S   N   G   I   T   Y   L   Y  W   Y   Q   Q
 CDR 1_____|

AAA CCG GGT AAA GCT CCG AAA CTG CTG ATC TAC CAG ATG TCT AAC CTG GCT AGC
 K   P   G   K   A   P   K   L   L   I   Y  |Q   M   S   N   L   A   S|
                                             ————— CDR 2 —————

GGC GTT CCT TCT CGT TTT TCT TCT AGC GGT AGC GGT ACT GAC TTC ACC CTG ACC
 G   V   P   S   R   F   S   S   S   G   S   G   T   D   F   T   L   T

ATT AGC TCT CTG CAG CCT GAA GAC TTT GCG ACC TAC TAT TGC GCT CAG AAC CTT
 I   S   S   L   Q   P   E   D   F   A   T   Y   Y   C  |A   Q   N   L
                                                         |————

GAA ATC CCG CGT ACC TTC GGC CAG GGT ACC AAA GTT GAA CTG AAG CGT ACC GTT
 E   I   P   R   T |F   G   Q   G   T   K   V   E   L   K   R   T   V
 CDR 3 _____|                         V_L End ---||-C_L Start GCG GCT CCG TCT GTT TTC ATC TTC CCA CCT AGC GAT GAA CAG CTT AAA TCT GGT
 A   A   P   S   V   F   I   F   P   P   S   D   E   Q   L   K   S   G ACT GCT AGC GTA GTT TGC CTG CTT AAC AAC TTC TAC CCT CGT GAA GCT AAA GTT
 T   A   S   V   V   C   L   L   N   N   F   Y   P   R   E   A   K   V CAG TGG AAA GTT GAC AAC GCT CTG CAG TCT GGT AAC TCT CAG GAA TCT GTG ACC
 Q   W   K   V   D   N   A   L   Q   S   G   N   S   Q   E   S   V   T GAA CAG GAT AGC AAA GAT AGC ACC TAT AGC CTG TCT AGC ACC CTG ACC CTT AGC
 E   Q   D   S   K   D   S   T   Y   S   L   S   S   T   L   T   L   S AAG GCG GAC TAT GAA AAA CAC AAA GTT TAC GCT TGC GAG GTG ACC CAC CAA GGT
 K   A   D   Y   E   K   H   K   V   Y   A   C   E   V   T   H   Q   G
```

FIGURE 2 (cont'd)

```
CTG TCT TCT CCG GTG ACT AAA TCC TTT AAC CGT GGC GAA TGC ACC CGT CAC CGT
 L   S   S   P   V   T   K   S   F   N   R   G   E   C   T   R   H   R
                                                 C_L End -------|  |--------------

CAG CCG CGT GGT TGG GAA CAG CTG TAT AAC ACC GTA TCT TTT AAC CTG GGT GAG
 Q   P   R   G   W   E   Q   L   Y   N   T   V   S   F   N   L   G   E
Furin linker ----------------|  |-------- de-bouganin Start GCG TAT GAA TAC CCG ACC TTC ATC CAG GAC CTG CGT AAT GAA CTT GCT AAA GGT
 A   Y   E   Y   P   T   F   I   Q   D   L   R   N   E   L   A   K   G ACC CCT GTT TGC CAG CTG CCT GTG ACC CTG CAG ACC ATC GCT GAT GAT AAA CGT
 T   P   V   C   Q   L   P   V   T   L   Q   T   I   A   D   D   K   R TTC GTT CTG GTT GAC ATT ACC ACC ACC TCC AAA AAA ACC GTT AAA GTC GCG ATC
 F   V   L   V   D   I   T   T   T   S   K   K   T   V   K   V   A   I GAT GTG ACC GAC GTT TAC GTG GTA GGT TAC CAG GAT AAA TGG GAC GGT AAA GAT
 D   V   T   D   V   Y   V   V   G   Y   Q   D   K   W   D   G   K   D CGT GCG GTT TTC CTG GAC AAA GTT CCG ACC GTA GCG ACT TCT AAA CTG TTC CCA
 R   A   V   F   L   D   K   V   P   T   V   A   T   S   K   L   F   P GGT GTG ACC AAC CGT GTG ACC CTG ACC TTC GAC GGC AGC TAT CAG AAA CTG GTT
 G   V   T   N   R   V   T   L   T   F   D   G   S   Y   Q   K   L   V AAC GCG GCC AAA GCT GAT CGT AAA GCT CTC GAA CTG GGT GTT AAC AAA CTG GAG
 N   A   A   K   A   D   R   K   A   L   E   L   G   V   N   K   L   E TTC AGC ATT GAA GCT ATC CAC GGT AAA ACC ATC AAC GGT CAA GAA GCA GCT AAA
 F   S   I   E   A   I   H   G   K   T   I   N   G   Q   E   A   A   K TTC TTC CTG ATC GTG ATC CAG ATG GTT AGC GAA GCA GCG CGT TTT AAA TAC ATT
 F   F   L   I   V   I   Q   M   V   S   E   A   A   R   F   K   Y   I GAA ACC GAA GTA GTT GAT CGT GGT CTG TAT GGT AGC TTC AAA CCG AAC TTC AAA
 E   T   E   V   V   D   R   G   L   Y   G   S   F   K   P   N   F   K GTT CTT AAC CTG GAG AAC AAC TGG GGT GAC ATT AGC GAC GCG ATC CAT AAA TCT
 V   L   N   L   E   N   N   W   G   D   I   S   D   A   I   H   K   S TCC CCG CAA TGC ACC ACC ATT AAC CCG GCT CTG CAG CTG ATC TCT CCG TCT AAC
 S   P   Q   C   T   T   I   N   P   A   L   Q   L   I   S   P   S   N GAT CCG TGG GTA GTT AAC AAA GTG TCT CAA ATC AGC CCG GAC ATG GGT ATC CTG
 D   P   W   V   V   N   K   V   S   Q   I   S   P   D   M   G   I   L AAA TTT AAA TCT AGC AAA TAG TGA CTC GAG
 K   F   K   S   S   K
de-bouganin End -------|
```

FIGURE 3

Optimized 845 Heavy Chain with Leader and RBS (SEQ ID NO 5 and 6):

```
AAGGA GAA TTC CATA ATG AAA TAT CTG CTG CCG ACT GCT GCT GCG GGT CTG CTG CTG
New RBS              M   K   Y   L   L   P   T   A   A   A   G   L   L   L
       |_____ PelB Leader Sequence _____

CTG GCT GCG CAA CCG GCT ATG GCT CAT CAC CAC CAC CAC CAT GAG GTT CAG CTG
 L   A   A   Q   P   A   M   A   H   H   H   H   H   H   E   V   Q   L
_____|        6xHis         |------V_H Start GTC CAG TCC GGT CCG GGT CTG GTT CAG CCG GGT GGT AGC GTT CGT ATT AGC TGC
 V   Q   S   G   P   G   L   V   Q   P   G   G   S   V   R   I   S   C GCG GCG AGC GGT TAC ACC TTC ACC AAC TAC GGT ATG AAC TGG GTT AAA CAG GCT
 A   A   S   G   Y   T   F   T   N   Y   G   M   N   W   V   K   Q   A
                                 |—————— CDR 1 ——————|

CCG GGT AAA GGT TTG GAA TGG ATG GGT TGG ATC AAC ACC TAT ACC GGT GAG TCT
 P   G   K   G   L   E   W   M   G   W   I   N   T   Y   T   G   E   S
                                     |——————————————————— CDR 2 ———————

ACC TAC GCT GAT AGC TTC AAA GGC CGT TTC ACC TTT AGC CTT GAC ACT TCT GCG
 T   Y   A   D   S   F   K   G   R   F   T   F   S   L   D   T   S   A
 ———————————————————————————————|

AGC GCG GCG TAC CTG CAG ATT AAC TCT CTG CGT GCT GAG GAC ACT GCG GTT TAC
 S   A   A   Y   L   Q   I   N   S   L   R   A   E   D   T   A   V   Y

TAC TGC GCT CGT TTC GCG ATC AAA GGT GAC TAT TGG GGT CAG GGT ACT CTG CTG
 Y   C   A   R   F   A   I   K   G   D   Y   W   G   Q   G   T   L   L
              |———————————— CDR3 ————————————|

ACC GTT AGC AGC GCT AGC ACT AAA GGT CCG TCC GTT TTC CCA CTG GCT CCG TCT
 T   V   S   S   A   S   T   K   G   P   S   V   F   P   L   A   P   S
V_H End --------||------- C_H Start TCT AAA AGC ACT TCT GGT GGT ACC GCG GCT CTG GGT TGC CTT GTT AAA GAC TAC
 S   K   S   T   S   G   G   T   A   A   L   G   C   L   V   K   D   Y TTC CCT GAA CCG GTC ACC GTT AGC TGG AAC TCC GGT GCG TTG ACC TCT GGT GTT
 F   P   E   P   V   T   V   S   W   N   S   G   A   L   T   S   G   V CAC ACC TTC CCA GCG GTT CTG CAG TCT AGC GGT CTG TAT AGC CTG AGC TCT GTA
 H   T   F   P   A   V   L   Q   S   S   G   L   Y   S   L   S   S   V GTT ACC GTT CCG TCT TCT AGC CTG GGT ACG CAG ACC TAC ATC TGC AAC GTG AAC
 V   T   V   P   S   S   S   L   G   T   Q   T   Y   I   C   N   V   N CAC AAA CCG AGC AAC ACT AAA GTG GAT AAA AAA GTT GAA CCG AAG TCT TGC TAG
 H   K   P   S   N   T   K   V   D   K   K   V   E   P   K   S   C
                                                                     C_H TGA TCT AGA GTC GAC CTG CAG GTC TAT GGA ACG ATA AAT GCC CAT GAA AAT TCT
end-|

ATT TCA AGG AGA CAG TCA TA ATG AAA TAC CTT CTG CCG ACC GCT GCC GCT GGT
```

FIGURE 4

Optimized 845 Light Chain with Leader and RBS (SEQ ID NO: 7 and 8)

```
AAGGA GAA TTC CATA ATG AAA TAT CTG CTG CCG ACT GCT GCT GCG GGT CTG CTG CTG
New RBS               M   K   Y   L   L   P   T   A   A   A   G   L   L   L
            |_____ PelB Leader Sequence _____

CTG GCT GCG CAA CCG GCT ATG GCT CAT CAC CAC CAC CAC CAT
 L   A   A   Q   P   A   M   A   H   H   H   H   H   H
_____|          6xHis

GAC ATC CAG ATG ACC CAG TCC
 D   I   Q   M   T   Q   S
V_L Start

CCG TCT AGC CTG AGC GCA AGC GTT GGT GAC CGT GTG ACC ATC ACC TGC CGT AGC
 P   S   S   L   S   A   S   V   G   D   R   V   T   I   T   C   R   S
                                                                 |—

ACT AAA TCC CTG CTG CAC TCT AAC GGC ATC ACC TAC CTG TAT TGG TAC CAA CAG
 T   K   S   L   L   H   S   N   G   I   T   Y   L   Y   W   Y   Q   Q
 CDR 1 ——————————————————————————————————————————————|

AAA CCG GGT AAA GCT CCG AAA CTG CTG ATC TAC CAG ATG TCT AAC CTG GCT AGC
 K   P   G   K   A   P   K   L   L   I   Y   Q   M   S   N   L   A   S
                                         |—————— CDR 2 ——————————|

GGC GTT CCT TCT CGT TTT TCT TCT AGC GGT AGC GGT ACT GAC TTC ACC CTG ACC
 G   V   P   S   R   F   S   S   S   G   S   G   T   D   F   T   L   T

ATT AGC TCT CTG CAG CCT GAA GAC TTT GCG ACC TAC TAT TGC GCT CAG AAC CTT
 I   S   S   L   Q   P   E   D   F   A   T   Y   Y   C   A   Q   N   L
                                                         |—

GAA ATC CCG CGT ACC TTC GGC CAG GGT ACC AAA GTT GAA CTG AAG CGT ACC GTT
 E   I   P   R   T   F   G   Q   G   T   K   V   E   L   K   R   T   V
CDR 3 ——————————————|                                V_L End ---||-C_L Start GCG GCT CCG TCT GTT TTC ATC TTC CCA CCT AGC GAT GAA CAG CTT AAA TCT GGT
 A   A   P   S   V   F   I   F   P   P   S   D   E   Q   L   K   S   G ACT GCT AGC GTA GTT TGC CTG CTT AAC AAC TTC TAC CCT CGT GAA GCT AAA GTT
 T   A   S   V   V   C   L   L   N   N   F   Y   P   R   E   A   K   V CAG TGG AAA GTT GAC AAC GCT CTG CAG TCT GGT AAC TCT CAG GAA TCT GTG ACC
 Q   W   K   V   D   N   A   L   Q   S   G   N   S   Q   E   S   V   T GAA CAG GAT AGC AAA GAT AGC ACC TAT AGC CTG TCT AGC ACC CTG ACC CTT AGC
 E   Q   D   S   K   D   S   T   Y   S   L   S   S   T   L   T   L   S AAG GCG GAC TAT GAA AAA CAC AAA GTT TAC GCT TGC GAG GTG ACC CAC CAA GGT
 K   A   D   Y   E   K   H   K   V   Y   A   C   E   V   T   H   Q   G CTG TCT TCT CCG GTG ACT AAA TCC TTT AAC CGT GGC GAA TGC TAG TGA CTC GAG
 L   S   S   P   V   T   K   S   F   N   R   G   E   C
                                    C_L End -------|
```

FIGURE 5

Optimized Bouganin with Leader and RBS (SEQ ID NO: 9 and 10)

```
AAGGA GAA TTC CATA ATG AAA TAT CTG CTG CCG ACT GCT GCT GCG GGT CTG CTG CTG
new RBS             M   K   Y   L   L   P   T   A   A   A   G   L   L   L
       |_____  PelB Leader Sequence_____

CTG GCT GCG CAA CCG GCT ATG GCT CAT CAC CAC CAC CAC CAT
 L   A   A   Q   P   A   M   A   H   H   H   H   H   H
_____|            6xHis

TAT AAC ACC GTA TCT TTT AAC CTG GGT GAG
 Y   N   T   V   S   F   N   L   G   E
|------- de-bouganin Start GCG TAT GAA TAC CCG ACC TTC ATC CAG GAC CTG CGT AAT GAA CTT GCT AAA GGT
 A   Y   E   Y   P   T   F   I   Q   D   L   R   N   E   L   A   K   G ACC CCT GTT TGC CAG CTG CCT GTG ACC CTG CAG ACC ATC GCT GAT GAT AAA CGT
 T   P   V   C   Q   L   P   V   T   L   Q   T   I   A   D   D   K   R TTC GTT CTG GTT GAC ATT ACC ACC ACC TCC AAA AAA ACC GTT AAA GTC GCG ATC
 F   V   L   V   D   I   T   T   T   S   K   K   T   V   K   V   A   I GAT GTG ACC GAC GTT TAC GTG GTA GGT TAC CAG GAT AAA TGG GAC GGT AAA GAT
 D   V   T   D   V   Y   V   V   G   Y   Q   D   K   W   D   G   K   D CGT GCG GTT TTC CTG GAC AAA GTT CCG ACC GTA GCG ACT TCT AAA CTG TTC CCA
 R   A   V   F   L   D   K   V   P   T   V   A   T   S   K   L   F   P GGT GTG ACC AAC CGT GTG ACC CTG ACC TTC GAC GGC AGC TAT CAG AAA CTG GTT
 G   V   T   N   R   V   T   L   T   F   D   G   S   Y   Q   K   L   V AAC GCG GCC AAA GCT GAT CGT AAA GCT CTC GAA CTG GGT GTT AAC AAA CTG GAG
 N   A   A   K   A   D   R   K   A   L   E   L   G   V   N   K   L   E TTC AGC ATT GAA GCT ATC CAC GGT AAA ACC ATC AAC GGT CAA GAA GCA GCT AAA
 F   S   I   E   A   I   H   G   K   T   I   N   G   Q   E   A   A   K TTC TTC CTG ATC GTG ATC CAG ATG GTT AGC GAA GCA GCG CGT TTT AAA TAC ATT
 F   F   L   I   V   I   Q   M   V   S   E   A   A   R   F   K   Y   I GAA ACC GAA GTA GTT GAT CGT GGT CTG TAT GGT AGC TTC AAA CCG AAC TTC AAA
 E   T   E   V   V   D   R   G   L   Y   G   S   F   K   P   N   F   K GTT CTT AAC CTG GAG AAC AAC TGG GGT GAC ATT AGC GAC GCG ATC CAT AAA TCT
 V   L   N   L   E   N   N   W   G   D   I   S   D   A   I   H   K   S TCC CCG CAA TGC ACC ACC ATT AAC CCG GCT CTG CAG CTG ATC TCT CCG TCT AAC
 S   P   Q   C   T   T   I   N   P   A   L   Q   L   I   S   P   S   N GAT CCG TGG GTA GTT AAC AAA GTG TCT CAA ATC AGC CCG GAC ATG GGT ATC CTG
 D   P   W   V   V   N   K   V   S   Q   I   S   P   D   M   G   I   L AAA TTT AAA TCT AGC AAA TAG TGA CTC GAG
 K   F   K   S   S   K
de-bouganin
```

FIGURE 6

Comparison of VB6-845 Original *(Or)* and Optimized (Op) Sequences
Nucleotide Changes are Shown in Bold on the Original Sequence VH-CH-OPTIMIZED / *VH-CH original*

VH (SEQ ID No 11 and 12)
(Op) GAG GTT CAG CTG GTC CAG TCC GGT CCG GGT CTG GTT CAG CCG GGT GGT AGC GTT
*(Or)* GAA GTA CAG CTG GTT CAG TCC GGC CCG GGT CTT GTT CAA CCG GGT GGT TCC GTT (Op) CGT ATT AGC TGC GCG GCG AGC GGT TAC ACC TTC ACC AAC TAC GGT ATG AAC TGG
*(Or)* CGT ATC TCT TGC GCT GCT TCT GGT TAC ACG TTC ACC AAC TAC GGC ATG AAC TGG (Op) GTT AAA CAG GCT CCG GGT AAA GGT TTG GAA TGG ATG GGT TGG ATC AAC ACC TAT
*(Or)* GTC AAA CAG GCT CCG GGT AAA GGC CTG GAA TGG ATG GGC TGG ATC AAC ACC TAC (Op) ACC GGT GAG TCT ACC TACGCT GAT AGC TTC AAA GGC CGT TTC ACC TTT AGC CTT
*(Or)* ACC GGT GAA TCC ACC TAC GCT GAC TCC TTC AAA GGT CGC TTC ACT TTC TCC CTC (Op) GAC ACT TCT GCG AGC GCG GCG TAC CTG CAG ATT AAC TCT CTG CGT GCT GAG GAC
*(Or)* GAC ACA AGT GCT AGT GCT GCA TAC CTC CAA ATC AAC TCG CTG CGT GCA GAG GAT (Op) ACT GCG GTT TAC TAC TGC GCT CGT TTC GCG ATC AAA GGT GAC TAT TGG GGT CAG
*(Or)* ACA GCA GTC TAT TAC TGC GCC CGT TTC GCT ATC AAA GGT GAC TAC TGG GGT CAA (Op) GGT ACT CTG CTG ACC GTT AGC AGC
*(Or)* GGC ACG CTG CTG ACC GTT TCC TCG

CH (SEQ ID NO 13 and 14)
(Op) GCT AGC ACT AAA GGT CCG TCC GTT TTC CCA CTG GCT CCG TCT TCT AAA AGC ACT
*(Or)* GCT AGC ACC AAA GGC CCA TCG GTC TTC CCC CTG GCA CCC TCC TCC AAG AGC ACC (Op) TCT GGT GGT ACC GCG GCT CTG GGT TGC CTT GTT AAA GAC TAC TTC CCT GAA CCG
*(Or)* TCT GGG GGC ACA GCG GCC CTG GGC TGC CTG GTC AAG GAC TAC TTC CCC GAA CCG (Op) GTC ACC GTT AGC TGG AAC TCC GGT GCG TTG ACC TCT GGT GTT CAC ACC TTC CCA
*(Or)* GTG ACG GTG TCG TGG AAC TCA GGC GCC CTG ACC AGC GGC GTG CAC ACC TTC CCG (Op) GCG GTT CTG CAG TCT AGC GGT CTG TAT AGC CTG AGC TCT GTA GTT ACC GTT CCG
*(Or)* GCT GTC CTA CAG TCC TCA GGA CTC TAC TCC CTC AGC AGC GTG GTG ACC GTG CCC (Op) TCT TCT AGC CTG GGT ACG CAG ACC TAC ATC TGC AAC GTG AAC CAC AAA CCG AGC
*(Or)* TCC AGC AGC TTG GGC ACC CAG ACC TAC ATC TGC ACC GTG AAT CAC AAG CCC AGC (Op) AAC ACT AAA GTG GAT AAA AAA GTT GAA CCG AAG TCT TGC TAG TGA
*(Or)* AAC ACC AAG GTG GAC AAG AAA GTT GAG CCC AAA TCT TGT TAG TGA

FIGURE 6 (cont'd)

VL-CL-OPTIMIZED/ VL-CL Original

VL (SEQ ID NO 15 and 16)
(Op) GAC ATC CAG ATG ACC CAG TCC CCG TCT AGC CTG AGC GCA AGC GTT GGT GAC CGT
(Or) GAT ATC CAG ATG ACC CAG TCC CCG TCC TCC CTG AGT GCT TCT GTT GGT GAC CGT (Op) GTG ACC ATC ACC TGC CGT AGC ACT AAA TCC CTG CTG CAC TCT AAC GGC ATC ACC
(Or) GTT ACC ATC ACC TGC CGT TCC ACC AAA TCC CTC CTG CAC TCC AAC GGT ATC ACC (Op) TAC CTG TAT TGG TAC CAA CAG AAA CCG GGT AAA GCT CCG AAA CTG CTG ATC TAC
(Or) TAC CTT TAT TGG TAT CAA CAG AAA CCG GGT AAA GCT CCG AAA CTT CTG ATC TAC (Op) CAG ATG TCT AAC CTG GCT AGC GGC GTT CCT TCT CGT TTT TCT TCT AGC GGT AGC
(Or) CAG ATG TCC AAC CTG GCT TCC GGT GTT CCG TCT CGT TTC TCC AGT TCT GGT TCT

(Op) GGT ACT GAC TTC ACC CTG ACC ATT AGC TCT CTG CAG CCT GAA GAC TTT GCG ACC
(Or) GGT ACC GAC TTC ACC CTG ACC ATC TCT TCT CTG CAG CCG GAA GAC TTC GCT ACC (Op) TAC TAT TGC GCT CAG AAC CTT GAA ATC CCG CGT ACC TTC GGC CAG GGT ACC AAA
(Or) TAC TAC TGC GCT CAG AAC CTG GAA ATC CCG CGT ACC TTC GGT CAG GGT ACC AAA (Op) GTT GAA CTG AAG CGT
(Or) GTT GAA CTT AAG CGC

CL (SEQ ID NO 17 and 18)
(Op) ACC GTT GCG GCT CCG TCT GTT TTC ATC TTC CCA CCT AGC GAT GAA CAG CTT AAA
(Or) ACT GTG GCT GCA CCA TCT GTC TTC ATC TTC CCG CCA TCT GAT GAG CAG TTG AAA (Op) TCT GGT ACT GCT AGC GTA GTT TGC CTG CTT AAC AAC TTC TAC CCT CGT GAA GCT
(Or) TCT GGA ACT GCC TCT GTT GTG TGC CTG CTG AAT AAC TTC TAT CCC AGA GAG GCC (Op) AAA GTT CAG TGG AAA GTT GAC AAC GCT CTG CAG TCT GGT AAC TCT CAG GAA TCT
(Or) AAA GTA CAG TGG AAG GTG GAT AAC GCC CTC CAA TCG GGT AAC TCC CAG GAG AGT

(Op) GTG ACC GAA CAG GAT AGC AAA GAT AGC ACC TAT AGC CTG TCT AGC ACC CTG ACC
(Or) GTC ACA GAG CAG GAC AGC AAG GAC AGC ACC TAC AGC CTC AGC AGC ACC CTG ACG (Op) CTT AGC AAG GCG GAC TAT GAA AAA CAC AAA GTT TAC GCT TGC GAG GTG ACC CAC
(Or) CTG AGC AAA GCA GAC TAC GAG AAA CAC AAA GTC TAC GCC TGC GAA GTC ACC CAT (Op) CAA GGT CTG TCT TCT CCG GTG ACT AAA TCC TTT AAC CGT GGC GAA TGC
(Or) CAG GGC CTG AGC TCG CCC GTC ACA AAG AGC TTC AAC AGG GGA GAG TGT

FIGURE 6 (cont'd)

Bouganin Optimized/ Bouganin Original (SEQ ID No 19 and 20)

```
(Op)TAT AAC ACC GTA TCT TTT AAC CTG GGT GAG GCG TAT GAA TAC CCG ACC TTC ATC
(Or)TAC AAC ACC GTG TCA TTT AAC CTT GGA GAA GCT TAT GAG TAC CCC ACT TTT ATA (Op)CAG GAC CTG CGT AAT GAA CTT GCT AAA GGT ACC CCT GTT TGC CAG CTG CCT GTG
(Or)CAA GAT TTG CGC AAT GAA TTG GCT AAG GGC ACA CCA GTA TGT CAA CTT CCA GTG (Op)ACC CTG CAG ACC ATC GCT GAT GAT AAA CGT TTC GTT CTG GTT GAC ATT ACC ACC
(Or)ACA CTA CAA ACC ATA GCC GAT GAC AAG CGA TTT GTT CTA GTT GAT ATC ACT ACG (Op)ACC TCC AAA AAA ACC GTT AAA GTC GCG ATC GAT GTG ACC GAC GTT TAC GTG GTA
(Or)ACC TCG AAG AAA ACA GTT AAG GTT GCT ATA GAT GTG ACA GAT GTG TAT GTT GTG (Op)GGT TAC CAG GAT AAA TGG GAC GGT AAA GAT CGT GCG GTT TTC CTG GAC AAA GTT
(Or)GGT TAT CAA GAC AAA TGG GAT GGC AAA GAT CGA GCT GTT TTC CTT GAC AAG GTT (Op)CCG ACC GTA GCG ACT TCT AAA CTG TTC CCA GGT GTG ACC AAC CGT GTG ACC CTG
(Or)CCT ACT GTT GCA ACT AGT AAA CTT TTC CCA GGG GTG ACT AAT CGT GTA ACG TTA (Op)ACC TTC GAC GGC AGC TAT CAG AAA CTG GTT AAC GCG GCC AAA GCT GAT CGT AAA
(Or)ACA TTT GAT GGC AGC TAT CAG AAA CTT GTG AAT GCT GCC AAA GCT GAT AGA AAG (Op)GCT CTC GAA CTG GGT GTT AAC AAA CTG GAG TTC AGC ATT GAA GCT ATC CAC GGT
(Or)GCT CTC GAA CTG GGG GTT AAC AAA TTG GAA TTT TCC ATT GAA GCA ATC CAT GGT (Op)AAA ACC ATC AAC GGT CAA GAA GCA GCT AAA TTC TTC CTG ATC GTG ATC CAG ATG
(Or)AAA ACG ATA AAT GGT CAA GAG GCA GCC AAG TTC TTT CTT ATT GTC ATC CAA ATG (Op)GTT AGC GAA GCA GCG CGT TTT AAA TAC ATT GAA ACC GAA GTA GTT GAT CGT GGT
(Or)GTT TCA GAG GCA GCT CGG TTC AAA TAT ATT GAG ACT GAG GTG GTT GAT AGA GGA (Op)CTG TAT GGT AGC TTC AAA CCG AAC TTC AAA GTT CTT AAC CTG GAG AAC AAC TGG
(Or)TTA TAT GGA TCA TTC AAA CCT AAT TTT AAA GTA TTG AAC TTG GAG AAC AAT TGG (Op)GGT GAC ATT AGC GAC GCG ATC CAT AAA TCT TCC CCG CAA TGC ACC ACC ATT AAC
(Or)GGC GAC ATC TCT GAT GCC ATT CAC AAA TCA TCC CCA CAA TGT ACC ACT ATT AAT (Op)CCG GCT CTG CAG CTG ATC TCT CCG TCT AAC GAT CCG TGG GTA GTT AAC AAA GTG
(Or)CCG GCA CTT CAG TTG ATA AGC CCC TCA AAT GAC CCA TGG GTT GTA AAT AAA GTG (Op)TCT CAA ATC AGC CCG GAC ATG GGT ATC CTG AAA TTT AAA TCT AGC AAA
(Or)AGT CAA ATT AGT CCC GAT ATG GGT ATC CTT AAG TTT AAA AGC TCC AAA
```

FIGURE 6 (cont'd)

First PelB and Initial Sequence including Histidines (SEQ ID NO 21 and 22)

(Op) GAA TTC ............... DELETED SEQUENCE FROM RBS..........................................................
(Or) GAA TTC CTG CAG GTC TAT GGA ACG ATA AAT GCC CAT GAA AAT TCT ATT TCA AGG (Op) ..................... CA TA ATG AAA TAT CTG CTG CCG ACT GCT GCT GCG GGT CTG CTG CTG
(Or) AGA CAG TCA TA ATG AAA TAC CTA TTG CCT ACG GCA GCC GCT GGA TTG TTA TTA (Op) CTG GCT GCG CAA CCG GCT ATG GCT CAT CAC CAC CAC CAC CAT
(Or) CTC GCT GCC CAA CCA GCG ATG GCG CAC CAT CAT CAC CAT CAC

Second Pel B leader and Intervening Sequence (SEQ ID NO 23 and 24)

(Op) TCT AGA GTC GAC CTG CAG GTC TAT GGA ACG ATA AAT GCC CAT GAA AAT TCT ATT
(Or) TCT AGA GTC GAC CTG CAG GTC TAT GGA ACG ATA AAT GCC CAT GAA AAT TCT ATT (Op) TCA AGG AGA CAG TCA TA ATG AAA TAC CTT CTG CCG ACC GCT GCC GCT GGT CTG
(Or) TCA AGG AGA CAG TCA TA ATG AAA TAC CTA TTG CCT ACG GCA GCC GCT GGA TTG (Op) CTG CTG TTG GCT GCT CAA CCG GCT ATG GCA
(Or) TTA TTA CTC GCT GCC CAA CCA GCG ATG GCG

Furin linker (SEQ ID NO 25 and 26)
(Op) ACC CGT CAC CGT CAG CCG CGT GGT TGG GAA CAG CTG
(Or) ACC AGG CAC AGG CAG CCC AGA GGC TGG GAG CAG CTC

BINDING PROTEINS THAT BIND TO EPCAM LINKED TO AN EFFECTOR MOLECULE

FIELD OF THE INVENTION

The invention relates to optimized nucleotide sequences for improved recombinant protein expression.

BACKGROUND OF THE INVENTION

VB6-845 is a recombinantly expressed therapeutic protein consisting of a monoclonal antibody specific for the cell surface protein EpCAM linked to a modified form of bouganin (WO 2005/090579 A1). VB6-845 is currently being produced using an *E. coli* based recombinant protein expression system.

This product and other Fab-bouganin fusion proteins are intended for systemic administration and it is expected that patients would receive around 0.1-1.0 grams of protein per dose of treatment. Under this regimen it was found that that it would be economically advantageous to modify the existing expression system which typically yielded less than 1-10 mg/L, in order to increase product yield.

During recombinant protein production in a heterologous system improper folding of the nascent protein is often the cause of decreased yield of functional protein. Different approaches have been taken to improve folding and expression, including the use of chaperons, changes to the fermentation conditions to affect rate of production and various forms of re-engineering of the expression vector. (Vasseur-Godbillon et al., 2006; Endo et al., 2006; Xu et al., 2005; Makrides, 1996; Baneyx et al., 1991).

SUMMARY OF THE INVENTION

The yield of expression of VB6-845 in an *E. coli* expression system was improved by modifying the coding and non-coding nucleotide sequence of the expression vector. More specifically, the modifications include removing major pauses in the open reading frame.

The resulting modified immunotoxin contains modifications in various regions in the nucleic acid sequence including the $V_H$ region, the $C_H$ region, the $V_L$ region, the $C_L$ region, the ribosome binding site (RBS), PelB leader sequence, the furin linker sequence as well as the bouganin toxin sequence. Accordingly, the invention relates to the entire modified immunotoxin as well as modified portions thereof which can be used separately in other applications for example, in the preparation of other immunotoxins.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 1 shows the original VB6-845 nucleotide and amino acid sequences (SEQ ID NOS:1 and 2).

FIG. 2 shows the optimized VB6-845 nucleotide and amino acid sequence with new RBS (SEQ ID NOS:3 and 4).

FIG. 3 shows the optimized 845 heavy chain with leader and RBS (SEQ ID NOS:5 and 6).

FIG. 4 shows the optimized 845 light chain with leader and RBS (SEQ ID NOS:7 and 8).

FIG. 5 shows the optimized bouganin with leader and RBS (SEQ ID NOS:9 and 10).

FIG. 6 shows the comparison of VB6-845 original (Or) and optimized (Op) sequences. Nucleotide changes are shown in bold on the original sequence.

DETAILED DESCRIPTION OF THE INVENTION

A. Definitions

Figure 7:
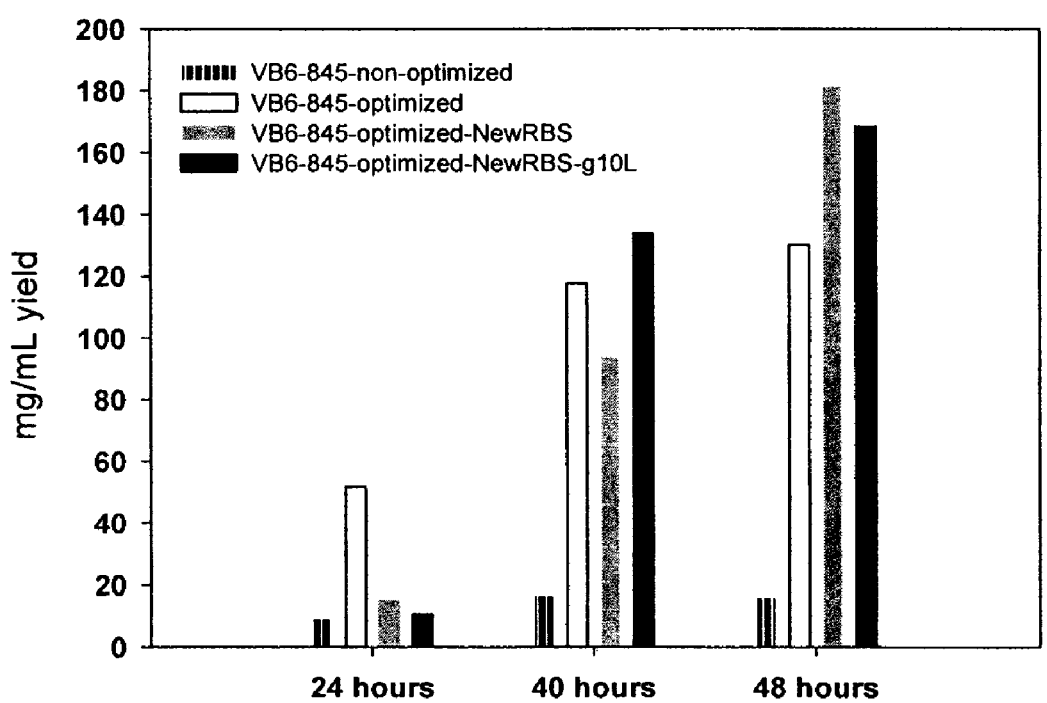
FIG. 7 is a graph showing the ELISA quantification of soluble VB6-845-de-bouganin protein in GMM medium. Supernatants of VB6-845-de-bouganin, VB6-845-de-bouganin-Optimized, VB6-845-de-bouganin-Optimized-NewRBS and VB6-845-de-bouganin-Optimized-NewRBS-g10L clones grown and induced in a fermentor containing GMM media were collected at 24, 40 and 48 hours post-induction and quantified by ELISA.

The term "antibody" as used herein is intended to include monoclonal antibodies, polyclonal antibodies, and chimeric antibodies such as humanized antibodies. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

The term "binding protein" as used herein refers to proteins that specifically bind to another substance such as an antigen. In an embodiment, binding proteins are antibodies or antibody fragments.

By "biologically compatible form suitable for administration in vivo" is meant a form of the substance to be administered in which any toxic effects are outweighed by the therapeutic effects.

As used herein, the phrase "effective amount" means an amount effective, at dosages and for periods of time necessary to achieve the desired result. Effective amounts of an immunoconjugate may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

The term "heavy chain variable region" as used herein refers to the variable region of a heavy chain of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus.

The term "immunoconjugate" as used herein comprises (1) a binding protein attached to (2) an effector molecule.

The term "immunotoxin" as used herein comprises (1) a binding protein attached to (2) a toxin.

The term "isolated nucleic acid sequences" as used herein refers to a nucleic acid substantially free of cellular material or culture medium when produced by recombinant DNA techniques.

The term "light chain variable region" as used herein refers to the variable region of a light chain of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

As used herein, the phrase "treating cancer" refers to inhibition of cancer cell replication, inhibition of cancer spread (metastasis), inhibition of tumor growth, reduction of cancer cell number or tumor growth, decrease in the malignant grade of a cancer (e.g., increased differentiation), or improved cancer-related symptoms.

B. Nucleic Acid Molecules

As mentioned previously, the nucleic acid sequences used to produce the VB6-845 immunotoxin were optimized which resulted in increased expression of the immunotoxin as described in the Examples. The present invention includes all of the novel, modified sequences. In particular, the invention includes the following nucleic acid sequences:

the $V_H$ region shown in SEQ ID NO:11 (FIG. 6);
the $C_H$ region shown in SEQ ID NO:13 (FIG. 6);
the $V_L$ region shown in SEQ ID NO:15 (FIG. 6);
the $C_L$ region shown in SEQ ID NO:17 (FIG. 6);
the heavy chain sequence with RBS and leader region shown in SEQ ID NO:5 (FIG. 3);
the light chain sequence with RBS and leader shown in SEQ ID NO:7 (FIG. 4);
the bouganin sequence with RBS and leader shown in SEQ ID NO:9 (FIG. 5);
the bouganin sequence shown in SEQ ID NO:19 (FIG. 6);
the VB6-845 sequence shown in SEQ ID NO:3 (FIG. 2);
the first PelB leader sequence and initial sequence including histidines optimized shown in SEQ ID NO:21 (FIG. 6);
the second PelB leader sequence and intervening sequence shown in SEQ ID NO:23 (FIG. 6); and
the furin linker sequence shown in SEQ ID NO:25 (FIG. 6).

The invention also includes expression vectors comprising one or more of the novel nucleic acid sequences as well as use of the expression vectors in the preparation of recombinant proteins.

C. Binding Proteins

The present invention also includes binding proteins encoded by the modified nucleic acid sequences of the invention.

In one aspect, the present invention provides a binding protein encoded by a nucleic acid molecule comprising one or more nucleic acid sequences selected from the group consisting of: the $V_H$ region shown in SEQ ID NO:11, the $C_H$ region shown in SEQ ID NO:13; the $V_L$ region shown in SEQ ID NO:15; and the $C_L$ region shown in SEQ ID NO:17.

In one embodiment, the binding protein comprises a modified heavy chain encoded by the nucleic acid sequence shown in SEQ ID NO:5 or having the amino acid sequence shown in SEQ ID NO:6.

In another embodiment, the binding protein comprises a modified light chain encoded by the nucleic acid sequence shown in SEQ ID NO:7 or having the amino acid sequence shown in SEQ ID NO:8.

The invention includes the use of the modified binding proteins in any and all applications including diagnostic and therapeutic applications.

D. Immunoconjugates

The invention includes the use of the binding proteins to prepare an immunoconjugate. Accordingly, the invention provides an immunoconjugate comprising (1) a binding protein of the invention, preferably an antibody or antibody fragment, attached to (2) an effector molecule. In one embodiment, the binding protein of the invention binds to an antigen or molecule on or in a cancer cell.

In one embodiment the effector molecule is (i) a label, which can generate a detectable signal, directly or indirectly, or (ii) a cancer therapeutic agent, which is either cytotoxic, cytostatic or otherwise prevents or reduces the ability of the cancer cells to divide and/or metastasize.

The effector molecule is preferably a cancer therapeutic agent. The cancer therapeutic agent is preferably a toxin that is either cytotoxic, cytostatic or otherwise prevents or reduces the ability of the cancer cells to divide and/or metastasize. Accordingly, one aspect of the invention is an immunoconjugate comprising (1) a binding protein of the invention, preferably an antibody or antibody fragment, attached to (2) a cancer therapeutic agent, such as a toxin.

In preferred embodiments, the toxin comprises a polypeptide having ribosome-inactivating activity including, without limitation, gelonin, bouganin, saporin, ricin, ricin A chain, bryodin, diphtheria toxin, restrictocin, *Pseudomonas* exotoxin A and variants thereof. When the protein is a ribosome-inactivating protein, the immunoconjugate must be internalized upon binding to the cancer cell in order for the toxin to be cytotoxic to the cells. Accordingly, in an embodiment of the invention, the effector molecule is a toxin and the immunoconjugate is internalized by the cancer cell.

In one embodiment of the invention, the toxin is bouganin or *Pseudomonas* exotoxin A, and variants thereof. In another embodiment, the toxin is modified bouganin or a truncated form of *Pseudomonas* exotoxin A that consists of amino acids 252-608. The modified bouganin includes de-bouganin which is also called deimmunized bouganin which is a bouganin that has been modified to reduce the propensity of the bouganin to elicit an immune response as described in WO 2005/090579.

In a preferred embodiment, the immunoconjugate comprises a modified bouganin encoded by a nucleic acid sequence shown in SEQ ID NO:19. In a preferred embodiment, the modified immunoconjugate has the nucleotide sequence shown in SEQ ID NO:3 or the amino acid sequence shown in SEQ ID NO:4.

The invention also includes the modified bouganin sequence shown in SEQ ID NO:19 and its use in the preparation of immunotoxins. Accordingly the invention comprises an immunotoxin comprising (1) a binding protein attached to (2) a bouganin encoded by the sequence shown in SEQ ID NO:19. The binding protein is preferably an antibody or antibody fragment that binds to a cancer associated antigen. In one embodiment, the cancer associated antigen is EpCAM, prostate specific antigen (PSA), prostate stem cell antigen (PSCA), mesothelin, CD25, EGFR (epidermal growth factor), high molecular weight melanoma associated antigen, CD22, a variant of mammalian Scratch (PCT/CA2006/002101), CD44E, a variant of mammalian alpha feto protein (AFP) (WO 2005/121341 A1), and a variant of Glut 8 (WO 2006/066408 A1).

The invention also provides a method of treating or preventing cancer, comprising administering to a patient suspected of having cancer an effective amount of the immunoconjugate of the invention, wherein the effector molecule is a cancer therapeutic agent. In another embodiment, the invention provides the use of an effective amount of the immunoconjugate of the invention, wherein the effector molecule is a cancer therapeutic agent, for the manufacture of a medicament for treating or preventing cancer. Furthermore, the invention provides the use of an effective amount of the immunoconjugate of the invention, wherein the effector molecule is a cancer therapeutic agent, comprising the use of an additional cancer therapeutic for the manufacture of a medicament for simultaneous, separate or sequential treatment or prevention of cancer.

In one embodiment of the invention, cancer includes, without limitation, cervical cancer, uterine cancer, ovarian cancer, pancreatic cancer, kidney cancer, gallbladder cancer, liver cancer, head and neck cancer, squamous cell carcinoma, gastrointestinal cancer, breast cancer (such as carcinoma, ductal, lobular, and nipple), prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, colon cancer, rectum cancer, stomach cancer, bladder cancer, pancreatic cancer, endometrial cancer, plasmacytoma, lymphoma, and melanoma. In a preferred embodiment, the cancer includes, without limitation, bladder cancer, breast cancer, cervical cancer, colon cancer, kidney cancer, liver cancer, lung cancer, ovarian cancer, pancreatic cancer, prostate cancer, rectal cancer, skin cancer, stomach cancer, uterine cancer, and head and neck cancer.

The ability of the immunoconjugate of the invention to selectively inhibit or destroy cancerous cells may be readily tested in vitro using cancer cell lines. The selective inhibitory effect of the immunoconjugates of the invention may be determined, for example by demonstrating the selective inhibition of cellular proliferation of the cancer cells.

Toxicity may also be measured based on cell viability, for example, the viability of cancer and normal cell cultures exposed to the immunoconjugate may be compared. Cell viability may be assessed by known techniques, such as trypan blue exclusion assays.

In another example, a number of models may be used to test the effectiveness of the immunoconjugates of the invention. Thompson, E. W. et al. (Breast Cancer Res. Treatment 31:357-370 (1994)) has described a model for the determination of invasiveness of human breast cancer cells in vitro by measuring tumor cell-mediated proteolysis of extracellular matrix and tumor cell invasion of reconstituted basement membrane (collagen, laminin, fibronectin, Matrigel or gelatin). Other applicable cancer cell models include cultured ovarian adenocarcinoma cells (Young, T. N. et al. Gynecol. Oncol. 62:89-99 (1996); Moore, D. H. et al. Gynecol. Oncol. 65:78-82 (1997)), human follicular thyroid cancer cells (Demeure, M. J. et al., World J. Surg. 16:770-776 (1992)), human melanoma (A-2058) and fibrosarcoma (HT-1080) cell lines (Mackay, A. R. et al. Lab. Invest. 70:781 783 (1994)), and lung squamous (HS-24) and adenocarcinoma (SB-3) cell lines (Spiess, E. et al. J. Histochem. Cytochem. 42:917-929 (1994)). An in vivo test system involving the implantation of tumors and measurement of tumor growth and metastasis in athymic nude mice has also been described (Thompson, E. W. et al., Breast Cancer Res. Treatment 31:357-370 (1994); Shi, Y. E. et al., Cancer Res. 53:1409-1415 (1993)).

The immunoconjugates of the invention may be formulated into pharmaceutical compositions for administration to subjects in a biologically compatible form suitable for administration in vivo. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the recombinant protein of the invention to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present invention provides a pharmaceutical composition for treating or preventing cancer comprising the immunoconjugates of the invention, and a pharmaceutically acceptable carrier, diluent or excipient. In a preferred embodiment, the effector molecule of the immunoconjugate in the pharmaceutical composition is a cancer therapeutic agent, more preferably a toxin.

The pharmaceutical preparation comprising the immunoconjugate of the invention may be administered systemically. The pharmaceutical preparation may be administered directly to the cancer site. Depending on the route of administration, the immunoconjugate may be coated in a material to protect the compound from the action of enzymes, acids and other natural conditions that may inactivate the compound.

In accordance with one aspect of the present invention, the immunoconjugate is delivered to the patient by direct administration. The invention contemplates the pharmaceutical composition being administered in at least an amount sufficient to achieve the endpoint, and if necessary, comprises a pharmaceutically acceptable carrier.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, alcohols, polyols, glycerin and vegetable oils, for example. Extemporaneous injection solutions and suspensions may be prepared from sterile powders, granules, tablets, or concentrated solutions or suspensions. Immunoconjugate may be supplied, for example but not by way of limitation, as a lyophilized powder which is reconstituted with sterile water or saline prior to administration to the patient.

E. Leader Sequences

The present invention also includes the modified leader sequences. In one embodiment, the modified leader sequence has the nucleotide sequence shown in SEQ ID NO:21 or 23 or the amino acid sequence shown in SEQ ID NO:22 or 24. Such leader sequences can be used to optimize the expression of other recombinant proteins including immunoconjugates as described above.

F. Linker Sequences

The present invention also includes modified linker sequences. In particular, the invention includes the modified furin linker sequences as shown in SEQ ID NO:25. The modified linker sequence can be used in the preparation of other conjugates including immunoconjugates, more preferably, immunotoxins.

The following non-limiting examples are illustrative of the present invention:

EXAMPLE 1

Evaluation of Improved Recombinant Expression

The expression level of VB6-845-de-bouganin-optimized clone was evaluated under optimal fermentation conditions. The clone was grown with high cell density in a fermentor containing GMM media and induced at an OD of 100. An ELISA was performed on supernatants collected at 24, 40, and 48 hours post-induction. Sequences of the original and optimized clones are shown in FIGS. 1 to 6.

Fed batch fermentation of VB6-845-Optimized clones was performed in a 20 L CHEMAP fermentor using GMM medium. A 2 L shake flask with 500 mL of GMM containing 25 µg/mL of tetracycline and supplemented with trace element D, calcium chloride, nicotinic acid and thiamine was inoculated with one vial of the MCB. The cells were placed in a shaking incubator set at 28° C. with a constant agitation of 200 rpm. The culture was grown until an $OD_{600}$ of 2.0-2.5 was attained. Then, 150 mL of the seed culture was used to inoculate a 20 L Chemap bioreactor containing 15 L of GMM media with supplement elements as described previously. The temperature was set at 28° C. and the pH maintained at 7.0 with the addition of a 50% ammonium hydroxide solution via the pH control loop throughout the entire fermentation. The agitation rate was set at 300 rpm with airflow of 3 slpm and incremented successively at 600 rpm and 6 slpm and then at 1000 rpm and 10 slpm to maintained the dissolved oxygen above 41% during the batch phase. When the carbon source of the batch media was exhausted, the dissolved oxygen increased above 90% which triggered the addition of feed 1 solution (50% glycerol solution). Then, the D0 setpoint was set at 41% and the feeding based on a cascade control of the DO reading. At an optical density of 100, the culture was induced by switching to feed 2 solution (50% glycerol+30 g/L arabinose solution) and the induction was carried out for 48 hours under the same control as the feed 1. At 24, 40 and 48 hours post-induction, 50 mL broth were centrifuged at 8000 rpm for 30 minutes at 2-8° C. and the supernatant collected and frozen at −20° C. for ELISA quantification.

An Immulon microtitre plate was coated overnight with 100 µL of rabbit anti-de-bouganin diluted at 10 µg/mL. After three washes with PBS/0.5° A) Tween 20, the plate was blocked with 1% BSA for 1 hour at room temperature. TB samples, 100 µL, diluted at 1/640 and 1/1280 and GMM samples at 1/12800 and 1/25600 were added to the plate and incubated for 2 hours at room temperature. Diluted, purified VB6-845 was used to generate the standard curve. VB6-845 at a known concentration and non-induced supernatant were used as positive and negative controls, respectively. After the incubation, the plate was washed as above and incubated with the second antibody, mouse anti-human IgG Fd diluted in 1/4000 in dilution buffer. After 1 hour incubation, the plate was washed and incubated with 100 µL of goat anti-mouse IgG (H+L) biotinylated diluted at 1/20000 for 1 hour at room temperature. Then, the plate was washed and 100 µL of streptavidin-HRP diluted at 1/1000 was added for 30 minutes at room temperature. The reaction was developed in presence of TMB substrate for 2 minutes and stopped with 1N phosphoric acid. The plate was read at a wavelength of 405 nm using the Softmax Pro software.

As seen in FIG. 7, 130 mg/mL of VB6-845-de-bouganin protein was detected in the supernatant after 48 hours post-induction of the optimized construct. In comparison, the non-optimized VB6-845-de-bouganin construct yields only 16 mg/mL under similar fermentation conditions. The VB6-845-de-bouganin-Optimized-NewRBS and VB6-845-de-bouganin-Optimized-NewRBS-g10L clones were also grown in GMM and the expressed protein quantified by ELISA. As expected, the levels of expression were higher than the VB6-845-de-bouganin-Optimized clone with 181 mg/mL for VB6-845-de-bouganin-Optimized-NewRBS clone and 168 mg/mL for VB6-845-de-bouganin-Optimized-NewRBS-g10L clone. In addition, in contrast to the VB6-845-de-bouganin-Optimized clone which seems to reach a plateau in expression after 48 hours, a plateau was not observed with the modified RBS clones. The expression of VB6-845-de-bouganin was increased a total of 11 times over the non-optimized clone by optimization of the nucleotide sequence and modification of the RBS. Since both de-bouganin and the conserved domain of the Fab have a eukaryotic origin, the usage codon of VB6-845-de-bouganin protein was optimized for improved expression in *E. coli* along with the removal of possible pause sequences or secondary structures of the mRNA. This led to 8 times increased expression of VB6-845-de-bouganin protein. The modification of the RBS site also led to a further increase of 30% expression of VB6-845-de-bouganin protein. The deleted region, between the EcoRI restriction site and the RBS from the original sequence, contained secondary structures which may have prevented the attachment of the rRNA complex. The deleted region also contained 3 ATG codons that can be used as initiation codons. The removal of these false initiations increased the efficient of the translation of VB6-845 protein.

EXAMPLE 2

Production of VB6-845 Optimized

Fermentation Media

Cultivation of *Escherichia coli* cells was performed in either 15 L or 1200 L bioreactor working volumes in glycerol minimal media (GMM) containing: ammonium sulfate (13 g/L), potassium phosphate monobasic (1.7 g/L), potassium phosphate dibasic (15 g/L), magnesium sulfate (0.3 g/L), biotin (0.0013 g/L), yeast extract (4.9 g/L), glycerol (19.8 g/L), and trace elements.

Fermentation Conditions

Fermentation was carried out in three distinct phase. The first phase, batch phase, occurred in the original cultivation media until carbon source exhaustion. At this point, fed-batch phase #1 was undertaken and consisted of pulse-addition of an aqueous solution containing 50% glycerol until an $OD_{600}$ 100 was achieved. Upon reaching of this OD, the fed-batch #2 induction phase was performed using L-arabinose (7 g/L) in an aqueous 50% glycerol solution. Throughout the fed-batch phases, the % DO was maintained between 20-50%

Optimization of Fermentation Induction Parameters for VB6-845 Expression

Initial fermentation conditions were predicated upon those implemented for the generation of other Fab-based molecules using a similar expression system. Experiments directed at evaluating the impact of fermentation parameters on expression of non optimized VB6-845 in the supernatant were carried out to identify conditions able to increase titers. Parameters were tested individually against the initial conditions, and the prominent ones able to increase expression were identified as: induction temperature, induction cell density, inducer concentration, and pH during the induction phase. The best condition identified for each parameter was combined to yield the "optimized fermentation conditions" under which non-optimized VB6-845 was expressed and analyzed in the supernatant. These conditions are summarized in Table 1.

Implementation of a combination of critical fermentation induction parameters raised expression levels of soluble VB6-845 in the culture supernatant to over 10-fold higher as compared against the original fermentation conditions. This fermentation process was scaled up to the 1200 L scale.

Scale-Up of VB6-845 Fermentation Process

Assessment of VB6-845 expression in the culture supernatant using separate clones containing expression vector before and after codon optimization including new RBS was carried at the 15 L bioreactor scale using the optimized fermentation conditions. Upon demonstration of significant increase in titers at this scale, the expression was evaluated at the 1200 L production scale. The results are summarized in Table 2. Expression of VB6-845 in the culture supernatant was increased to 100 mg/L at the 15 L scale upon codon optimization with the inclusion of the new RBS and represents a further 10-fold increase in titers and expression at 1200 L was determined to be 90 mg/L, yielding an overall 7-fold increase in VB6-845 titers.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Optimization of high cell density *E. coli* fermentation conditions in GMM to generate VB6-845 in culture supernatant (15 L bioreactor).

| Parameter | Initial fermentation conditions | Optimized fermentation conditions |
| --- | --- | --- |
| Induction temperature | 32° C. | 28° C. |
| Inducer concentration | 60 g/L | 6 g/L |
| Induction cell density | 50 | 100 |
| pH | 6.0 | 7.0 |
| VB6-845 titers | <1 mg/L | 10 mg/L |

TABLE 2

High cell density *E. coli* cultivation of optimized VB6-845 (15 L and 1200 L bioreactor). VB6-845 titers in culture supernatant (mg/L)

| Prior to codon optimization | | After codon optimization | |
| --- | --- | --- | --- |
| 15 L scale | 1200 L scale | 15 L scale | 1200 L scale |
| 10 | 12 | 110 | 90 |

FULL CITATIONS FOR REFERENCES REFERRED TO IN THE SPECIFICATION

Baneyx, F., Ayling, A., Palumbo, T., Thomas, D., and Georgiou, G. (1991). Optimization of growth conditions for the production of proteolytically-sensitive proteins in the periplasmic space of *Escherichia coli*. Appl. Microbiol. Biotechnol. 36, 14-20.

Endo, S., Tomimoto, Y., Shimizu, H., Taniguchi, Y., and Onizuka, T. (2006). Effects of *E. coli* Chaperones on the Solubility of Human Receptors in an In Vitro Expression System. Mol. Biotechnol. 33, 199-210.

Makrides, S. C. (1996). Strategies for achieving high-level expression of genes in *Escherichia coli*. Microbiol. Rev. 60, 512-538.

Vasseur-Godbillon, C., Hamdane, D., Marden, M. C., and Baudin-Creuza, V. (2006). High-yield expression in *Escherichia coli* of soluble human alpha-hemoglobin complexed with its molecular chaperone. Protein Eng Des Sel 19, 91-97.

Xu, H. M., Zhang, G. Y., Ji, X. D., Cao, L., Shu, L., and Hua, Z. C. (2005). Expression of soluble, biologically active recombinant human endostatin in *Escherichia coli*. Protein Expr. Purif. 41, 252-258.

The invention claimed is:

1. An isolated binding protein comprising a heavy chain and a light chain encoded by a nucleic acid molecule comprising a $V_H$ region shown in SEQ ID NO:11, a $C_H$ region shown in SEQ ID NO:13; a $V_L$ region shown in SEQ ID NO:15; and a $C_L$ region shown in SEQ ID NO:17.

2. The isolated binding protein according to claim 1 wherein the heavy chain is encoded by the nucleic acid sequence shown in SEQ ID NO:5.

3. The isolated binding protein according to claim 1 wherein the light chain is encoded by the nucleic acid sequence shown in SEQ ID NO:7.

4. An immunoconjugate comprising: (a) a binding protein according to claim 1 linked to (b) an effector molecule.

5. The immunoconjugate according to claim 4 wherein the effector molecule is a toxin.

6. The immunoconjugate according to claim 5 wherein the toxin is bouganin.

7. The immunoconjugate according to claim 1 wherein the bouganin is encoded by the nucleic acid sequence shown in SEQ ID NO:19.

8. The immunoconjugate according to claim 7 wherein the immunotoxin has a nucleic acid sequence shown in SEQ ID NO:3.

* * * * *

SEQUENCE LISTING

```
<160> NUMBER OF SEQ ID NOS: 26

<210> SEQ ID NO 1
<211> LENGTH: 2404
<212> TYPE: DNA
<213> ORGANISM: Artificial Sequence
<220> FEATURE:
<223> OTHER INFORMATION: Nucleotide sequence of unoptimized VB6-845

<400> SEQUENCE: 1
gaattcctgc aggtctatgg aacgataaat gcccatgaaa attctatttc aaggagacag      60
```

```
tcataatgaa ataccuattg cctacggcag ccgctggatt gttattactc gctgcccaac    120
cagcgatggc gcaccatcat caccatcacg aagtacagct ggttcagtcc ggcccgggtc    180
ttgttcaacc gggtggttcc gttcgtatct cttgcgctgc ttctggttac acgttcacca    240
actacggcat gaactgggtc aaacaggctc cgggtaaagg cctggaatgg atgggctgga    300
tcaacaccta caccggtgaa tccacctacg ctgactcctt caaaggtcgc ttcactttct    360
ccctcgacac aagtgctagt gctgcatacc tccaaatcaa ctcgctgcgt gcagaggata    420
cagcagtcta ttactgcgcc cgtttcgcta tcaaaggtga ctactgggt caaggcacgc    480 tgctgaccgt ttcctcggct agcaccaaag gcccatcggt cttcccctg gcaccctcct    540 ccaagagcac ctctggggc acagcggcc tgggctgcct ggtcaaggac tacttcccg    600 aaccggtgac ggtgtcgtgg aactcaggcg ccctgaccag cggcgtgcac accttcccgg    660
ctgtcctaca gtcctcagga ctctactccc tcagcagcgt ggtgaccgtg ccctccagca    720
gcttgggcac ccagacctac atctgcaacg tgaatcacaa gcccagcaac accaaggtgg    780
acaagaaagt tgagcccaaa tcttgttagt gatctagagt cgacctgcag gtctatggaa    840
cgataaatgc ccatgaaaat tctatttcaa ggagacagtc ataatgaaat acctattgcc    900
tacggcagcc gctggattgt tattactcgc tgcccaacca gcgatggcgg atatccagat    960
gacccagtcc ccgtcctccc tgagtgcttc tgttggtgac cgtgttacca tcacctgccg   1020
ttccaccaaa tccctcctgc actccaacgg tatcacctac ctttattggt atcaacagaa   1080
accgggtaaa gctccgaaac ttctgatcta ccagatgtcc aacctggctt ccggtgttcc   1140
gtctcgtttc tccagttctg gttctggtac cgacttcacc ctgaccatct cttctctgca   1200
gccggaagac ttcgctacct actactgcgc tcagaacctg gaaatcccgc gtaccttcgg   1260
tcagggtacc aaagttgaac ttaagcgcac tgtggctgca ccatctgtct tcatcttccc   1320
gccatctgat gagcagttga aatctggaac tgcctctgtt gtgtgcctgc tgaataactt   1380
ctatcccaga gaggccaaag tacagtggaa ggtggataac gccctccaat cgggtaactc   1440
ccaggagagt gtcacagagc aggacagcaa ggacagcacc tacagcctca gcagcaccct   1500
gacgctgagc aaagcagact acgagaaaca caaagtctac gcctgcgaag tcacccatca   1560
gggcctgagc tcgcccgtca caaagagctt caacagggga gagtgtacca ggcacaggca   1620
gcccagaggc tgggagcagc tctacaacac cgtgtcattt aaccttggag aagcttatga   1680
gtaccccact tttatacaag atttgcgcaa tgaattggct aagggcacac cagtatgtca   1740
acttccagtg acactacaaa ccatagccga tgacaagcga tttgttctag ttgatatcac   1800
tacgacctcg aagaaaacag ttaaggttgc tatagatgtg acagatgtgt atgttgtggg   1860
ttatcaagac aaatgggatg gcaaagatcg agctgttttc cttgacaagg ttcctactgt   1920
tgcaactagt aaacttttcc cagggtgac taatcgtgta acgttaacat tgatggcag   1980 ctatcagaaa cttgtgaatg ctgccaaagc tgatagaaag gctctcgaac tggggggttaa   2040 caaattggaa ttttccattg aagcaatcca tggtaaaacg ataaatggtc aagaggcagc   2100
caagttcttt cttattgtca tccaaatggt ttcagaggca gctcggttca aatatattga   2160
gactgaggtg gttgatagag gattatatgg atcattcaaa cctaatttta agtattgaa   2220 cttggagaac aattggggcg acatctctga tgccattcac aaatcatccc cacaatgtac   2280
cactattaat ccggcacttc agttgataag cccctcaaat gacccatggg ttgtaaataa   2340
agtgagtcaa attagtcccg atatgggtat ccttaagttt aaaagctcca atagtgact   2400 cgag                                                               2404
```

<210> SEQ ID NO 2
<211> LENGTH: 750
<212> TYPE: PRT
<213> ORGANISM: Artificial Sequence
<220> FEATURE:
<223> OTHER INFORMATION: Amino Acid sequence of unoptimized VB6-845

<400> SEQUENCE: 2

```
Met Lys Tyr Leu Leu Pro Thr Ala Ala Ala Gly Leu Leu Leu Ala
1               5                   10                  15

Ala Gln Pro Ala Met Ala His His His His His Glu Val Gln Leu
                20                  25                  30

Val Gln Ser Gly Pro Gly Leu Val Gln Pro Gly Gly Ser Val Arg Ile
            35                  40                  45

Ser Cys Ala Ala Ser Gly Tyr Thr Phe Thr Asn Tyr Gly Met Asn Trp
        50                  55                  60

Val Lys Gln Ala Pro Gly Lys Gly Leu Glu Trp Met Gly Trp Ile Asn
65                  70                  75                  80

Thr Tyr Thr Gly Glu Ser Thr Tyr Ala Asp Ser Phe Lys Gly Arg Phe
                85                  90                  95

Thr Phe Ser Leu Asp Thr Ser Ala Ser Ala Ala Tyr Leu Gln Ile Asn
            100                 105                 110

Ser Leu Arg Ala Glu Asp Thr Ala Val Tyr Tyr Cys Ala Arg Phe Ala
        115                 120                 125

Ile Lys Gly Asp Tyr Trp Gly Gln Gly Thr Leu Leu Thr Val Ser Ser
130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Met Lys Tyr Leu Leu Pro Thr Ala Ala
                245                 250                 255

Ala Gly Leu Leu Leu Leu Ala Ala Gln Pro Ala Met Ala Asp Ile Gln
            260                 265                 270

Met Thr Gln Ser Pro Ser Ser Leu Ser Ala Ser Val Gly Asp Arg Val
        275                 280                 285

Thr Ile Thr Cys Arg Ser Thr Lys Ser Leu Leu His Ser Asn Gly Ile
290                 295                 300

Thr Tyr Leu Tyr Trp Tyr Gln Gln Lys Pro Gly Lys Ala Pro Lys Leu
305                 310                 315                 320

Leu Ile Tyr Gln Met Ser Asn Leu Ala Ser Gly Val Pro Ser Arg Phe
                325                 330                 335

Ser Ser Ser Gly Ser Gly Thr Asp Phe Thr Leu Thr Ile Ser Ser Leu
            340                 345                 350

Gln Pro Glu Asp Phe Ala Thr Tyr Tyr Cys Ala Gln Asn Leu Glu Ile
        355                 360                 365
```

```
Pro Arg Thr Phe Gly Gln Gly Thr Lys Val Glu Leu Lys Arg Thr Val
    370                 375                 380

Ala Ala Pro Ser Val Phe Ile Phe Pro Pro Ser Asp Glu Gln Leu Lys
385                 390                 395                 400

Ser Gly Thr Ala Ser Val Val Cys Leu Leu Asn Asn Phe Tyr Pro Arg
                405                 410                 415

Glu Ala Lys Val Gln Trp Lys Val Asp Asn Ala Leu Gln Ser Gly Asn
            420                 425                 430

Ser Gln Glu Ser Val Thr Glu Gln Asp Ser Lys Asp Ser Thr Tyr Ser
        435                 440                 445

Leu Ser Ser Thr Leu Thr Leu Ser Lys Ala Asp Tyr Glu Lys His Lys
    450                 455                 460

Val Tyr Ala Cys Glu Val Thr His Gln Gly Leu Ser Ser Pro Val Thr
465                 470                 475                 480

Lys Ser Phe Asn Arg Gly Glu Cys Thr Arg His Arg Gln Pro Arg Gly
                485                 490                 495

Trp Glu Gln Leu Tyr Asn Thr Val Ser Phe Asn Leu Gly Glu Ala Tyr
            500                 505                 510

Glu Tyr Pro Thr Phe Ile Gln Asp Leu Arg Asn Glu Leu Ala Lys Gly
        515                 520                 525

Thr Pro Val Cys Gln Leu Pro Val Thr Leu Gln Thr Ile Ala Asp Asp
    530                 535                 540

Lys Arg Phe Val Leu Val Asp Ile Thr Thr Thr Ser Lys Lys Thr Val
545                 550                 555                 560

Lys Val Ala Ile Asp Val Thr Asp Val Tyr Val Val Gly Tyr Gln Asp
                565                 570                 575

Lys Trp Asp Gly Lys Asp Arg Ala Val Phe Leu Asp Lys Val Pro Thr
            580                 585                 590

Val Ala Thr Ser Lys Leu Phe Pro Gly Val Thr Asn Arg Val Thr Leu
        595                 600                 605

Thr Phe Asp Gly Ser Tyr Gln Lys Leu Val Asn Ala Ala Lys Ala Asp
    610                 615                 620

Arg Lys Ala Leu Glu Leu Gly Val Asn Lys Leu Glu Phe Ser Ile Glu
625                 630                 635                 640

Ala Ile His Gly Lys Thr Ile Asn Gly Gln Glu Ala Ala Lys Phe Phe
                645                 650                 655

Leu Ile Val Ile Gln Met Val Ser Glu Ala Ala Arg Phe Lys Tyr Ile
            660                 665                 670

Glu Thr Glu Val Val Asp Arg Gly Leu Tyr Gly Ser Phe Lys Pro Asn
        675                 680                 685

Phe Lys Val Leu Asn Leu Glu Asn Asn Trp Gly Asp Ile Ser Asp Ala
690                 695                 700

Ile His Lys Ser Ser Pro Gln Cys Thr Thr Ile Asn Pro Ala Leu Gln
705                 710                 715                 720

Leu Ile Ser Pro Ser Asn Asp Pro Trp Val Val Asn Lys Val Ser Gln
                725                 730                 735

Ile Ser Pro Asp Met Gly Ile Leu Lys Phe Lys Ser Ser Lys
            740                 745                 750

<210> SEQ ID NO 3
<211> LENGTH: 2354
<212> TYPE: DNA
<213> ORGANISM: Artificial Sequence
<220> FEATURE:
<223> OTHER INFORMATION: Nucleotide sequence of optimized VB6-845
```

-continued

```
<400> SEQUENCE: 3
aaggagaatt ccataatgaa atatctgctg ccgactgctg ctgcgggtct gctgctgctg      60
gctgcgcaac cggctatggc tcatcaccac caccaccatg aggttcagct ggtccagtcc     120
ggtccgggtc tggttcagcc gggtggtagc gttcgtatta gctgcgcggc gagcggttac     180
accttcacca actacggtat gaactgggtt aaacaggctc cgggtaaagg tttggaatgg     240
atgggttgga tcaacaccta taccggtgag tctacctacg ctgatagctt caaaggccgt     300 ttcacctttta gccttgacac ttctgcgagc gcggcgtacc tgcagattaa ctctctgcgt     360
gctgaggaca ctgcggttta ctactgcgct cgtttcgcga tcaaaggtga ctattggggt     420
cagggtactc tgctgaccgt tagcagcgct agcactaaag gtccgtccgt tttcccactg     480
gctccgtctt ctaaaagcac ttctggtggt accgcggctc tgggttgcct tgttaaagac     540
tacttccctg aaccggtcac cgttagctgg aactccggtg cgttgacctc tggtgttcac     600
accttcccag cggttctgca gtctagcggt ctgtatagcc tgagctctgt agttaccgtt     660
ccgtcttcta gcctgggtac gcagacctac atctgcaacg tgaaccacaa accgagcaac     720
actaaagtgg ataaaaaagt tgaaccgaag tcttgctagt gatctagagt cgacctgcag     780
gtctatggaa cgataaatgc ccatgaaaat tctatttcaa ggagacagtc ataatgaaat     840
accttctgcc gaccgctgcc gctggtctgc tgctgttggc tgctcaaccg gctatggcag     900
acatccagat gacccagtcc ccgtctagcc tgagcgcaag cgttggtgac cgtgtgacca     960
tcacctgccg tagcactaaa tccctgctgc actctaacgg catcacctac ctgtattggt    1020
accaacagaa accgggtaaa gctccgaaac tgctgatcta ccagatgtct aacctggcta    1080
gcggcgttcc ttctcgtttt tcttctagcg gtagcggtac tgacttcacc ctgaccatta    1140
gctctctgca gcctgaagac tttgcgacct actattgcgc tcagaacctt gaaatcccgc    1200
gtaccttcgg ccagggtacc aaagttgaac tgaagcgtac cgttgcggct ccgtctgttt    1260
tcatcttccc acctagcgat gaacagctta aatctgtac tgctagcgta gtttgcctgc     1320
ttaacaactt ctaccctcgt gaagctaaag ttcagtggaa agttgacaac gctctgcagt    1380
ctggtaactc tcaggaatct gtgaccgaac aggatagcaa agatagcacc tatagcctgt    1440
ctagcaccct gaccttagc aaggcggact atgaaaaaca caaagtttac gcttgcgagg    1500
tgacccacca aggtctgtct ctccggtga ctaaatcctt taaccgtggc gaatgcaccc     1560
gtcaccgtca gccgcgtggt tgggaacagc tgtataacac cgtatctttt aacctgggtg    1620
aggcgtatga atacccgacc ttcatccagg acctgcgtaa tgaacttgct aaaggtaccc    1680
ctgtttgcca gctgcctgtg accctgcaga ccatcgctga tgataaacgt ttcgttctgg    1740
ttgacattac caccacctcc aaaaaaaccg ttaaagtcgc gatcgatgtg accgacgttt    1800
acgtggtagg ttaccaggat aaatgggacg gtaaagatcg tgcggttttc ctggacaaag    1860
ttccgaccgt agcgacttct aaactgttcc caggtgtgac caaccgtgtg accctgacct    1920
tcgacggcag ctatcagaaa ctggttaacg cggccaaagc tgatcgtaaa gctctcgaac    1980
tgggtgttaa caaactggag ttcagcattg aagctatcca cggtaaaacc atcaacggtc    2040
aagaagcagc taaattcttc ctgatcgtga tccagatggt tagcgaagca gcgcgttttta    2100 aatacattga aaccgaagta gttgatcgtg gtctgtatgg tagcttcaaa ccgaacttca    2160
aagttcttaa cctggagaac aactgggtg acattagcga cgcgatccat aaatcttccc    2220
cgcaatgcac caccattaac ccggctctgc agctgatctc tccgtctaac gatccgtggg    2280
tagttaacaa agtgtctcaa atcagcccgg acatgggtat cctgaaattt aaatctagca    2340
```
aatagtgact cgag                                                       2354

<210> SEQ ID NO 4
<211> LENGTH: 750
<212> TYPE: PRT
<213> ORGANISM: Artificial Sequence
<220> FEATURE:
<223> OTHER INFORMATION: Amino Acid sequence of optimized VB6-845

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala His His His His His His Glu Val Gln Leu
            20                  25                  30

Val Gln Ser Gly Pro Gly Leu Val Gln Pro Gly Gly Ser Val Arg Ile
        35                  40                  45

Ser Cys Ala Ala Ser Gly Tyr Thr Phe Thr Asn Tyr Gly Met Asn Trp
    50                  55                  60

Val Lys Gln Ala Pro Gly Lys Gly Leu Glu Trp Met Gly Trp Ile Asn
65                  70                  75                  80

Thr Tyr Thr Gly Glu Ser Thr Tyr Ala Asp Ser Phe Lys Gly Arg Phe
                85                  90                  95

Thr Phe Ser Leu Asp Thr Ser Ala Ser Ala Ala Tyr Leu Gln Ile Asn
            100                 105                 110

Ser Leu Arg Ala Glu Asp Thr Ala Val Tyr Tyr Cys Ala Arg Phe Ala
        115                 120                 125

Ile Lys Gly Asp Tyr Trp Gly Gln Gly Thr Leu Leu Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Met Lys Tyr Leu Leu Pro Thr Ala Ala
                245                 250                 255

Ala Gly Leu Leu Leu Leu Ala Ala Gln Pro Ala Met Ala Asp Ile Gln
            260                 265                 270

Met Thr Gln Ser Pro Ser Ser Leu Ser Ala Ser Val Gly Asp Arg Val
        275                 280                 285

Thr Ile Thr Cys Arg Ser Thr Lys Ser Leu Leu His Ser Asn Gly Ile
    290                 295                 300

Thr Tyr Leu Tyr Trp Tyr Gln Gln Lys Pro Gly Lys Ala Pro Lys Leu
305                 310                 315                 320

Leu Ile Tyr Gln Met Ser Asn Leu Ala Ser Gly Val Pro Ser Arg Phe
                325                 330                 335

Ser Ser Ser Gly Ser Gly Thr Asp Phe Thr Leu Thr Ile Ser Ser Leu
            340                 345                 350

Gln Pro Glu Asp Phe Ala Thr Tyr Tyr Cys Ala Gln Asn Leu Glu Ile
        355                 360                 365

Pro Arg Thr Phe Gly Gln Gly Thr Lys Val Glu Leu Lys Arg Thr Val
    370                 375                 380

Ala Ala Pro Ser Val Phe Ile Phe Pro Pro Ser Asp Glu Gln Leu Lys
385                 390                 395                 400

Ser Gly Thr Ala Ser Val Val Cys Leu Leu Asn Asn Phe Tyr Pro Arg
                405                 410                 415

Glu Ala Lys Val Gln Trp Lys Val Asp Asn Ala Leu Gln Ser Gly Asn
            420                 425                 430

Ser Gln Glu Ser Val Thr Glu Gln Asp Ser Lys Asp Ser Thr Tyr Ser
        435                 440                 445

Leu Ser Ser Thr Leu Thr Leu Ser Lys Ala Asp Tyr Glu Lys His Lys
    450                 455                 460

Val Tyr Ala Cys Glu Val Thr His Gln Gly Leu Ser Ser Pro Val Thr
465                 470                 475                 480

Lys Ser Phe Asn Arg Gly Glu Cys Thr Arg His Arg Gln Pro Arg Gly
                485                 490                 495

Trp Glu Gln Leu Tyr Asn Thr Val Ser Phe Asn Leu Gly Glu Ala Tyr
            500                 505                 510

Glu Tyr Pro Thr Phe Ile Gln Asp Leu Arg Asn Glu Leu Ala Lys Gly
        515                 520                 525

Thr Pro Val Cys Gln Leu Pro Val Thr Leu Gln Thr Ile Ala Asp Asp
    530                 535                 540

Lys Arg Phe Val Leu Val Asp Ile Thr Thr Thr Ser Lys Lys Thr Val
545                 550                 555                 560

Lys Val Ala Ile Asp Val Thr Asp Val Tyr Val Val Gly Tyr Gln Asp
                565                 570                 575

Lys Trp Asp Gly Lys Asp Arg Ala Val Phe Leu Asp Lys Val Pro Thr
            580                 585                 590

Val Ala Thr Ser Lys Leu Phe Pro Gly Val Thr Asn Arg Val Thr Leu
        595                 600                 605

Thr Phe Asp Gly Ser Tyr Gln Lys Leu Val Asn Ala Ala Lys Ala Asp
    610                 615                 620

Arg Lys Ala Leu Glu Leu Gly Val Asn Lys Leu Glu Phe Ser Ile Glu
625                 630                 635                 640

Ala Ile His Gly Lys Thr Ile Asn Gly Gln Glu Ala Ala Lys Phe Phe
                645                 650                 655

Leu Ile Val Ile Gln Met Val Ser Glu Ala Ala Arg Phe Lys Tyr Ile
            660                 665                 670

Glu Thr Glu Val Val Asp Arg Gly Leu Tyr Gly Ser Phe Lys Pro Asn
        675                 680                 685

Phe Lys Val Leu Asn Leu Glu Asn Asn Trp Gly Asp Ile Ser Asp Ala
    690                 695                 700

Ile His Lys Ser Ser Pro Gln Cys Thr Thr Ile Asn Pro Ala Leu Gln
705                 710                 715                 720

Leu Ile Ser Pro Ser Asn Asp Pro Trp Val Val Asn Lys Val Ser Gln
                725                 730                 735

Ile Ser Pro Asp Met Gly Ile Leu Lys Phe Lys Ser Ser Lys
            740                 745                 750

<210> SEQ ID NO 5
<211> LENGTH: 866
<212> TYPE: DNA
<213> ORGANISM: Artificial Sequence
<220> FEATURE:
<223> OTHER INFORMATION: Nucleotide sequence of optimized VB6-845 heavy chain with RBS and leader

<400> SEQUENCE: 5

```
aaggagaatt ccataatgaa atatctgctg ccgactgctg ctgcgggtct gctgctgctg    60
gctgcgcaac cggctatggc tcatcaccac caccaccatg aggttcagct ggtccagtcc   120
ggtccgggtc tggttcagcc gggtggtagc gttcgtatta gctgcgcggc gagcggttac   180
accttcacca actacggtat gaactgggtt aaacaggctc cgggtaaagg tttggaatgg   240
atgggttgga tcaacaccta taccggtgag tctacctacg ctgatagctt caaaggccgt   300
ttcaccttta gccttgacac ttctgcgagc cggcgtacc tgcagattaa ctctctgcgt    360
gctgaggaca ctgcggttta ctactgcgct cgtttcgcga tcaaggtga ctattgggt     420
cagggtactc tgctgaccgt tagcagcgct agcactaaag gtccgtccgt tttcccactg   480
gctccgtctt ctaaaagcac ttctggtggt accgcggctc tgggttgcct tgttaaagac   540
tacttccctg aaccggtcac cgttagctgg aactccggtg cgttgacctc tggtgttcac   600
accttcccag cggttctgca gtctagcggt ctgtatagcc tgagctctgt agttaccgtt   660
ccgtcttcta gcctgggtac gcagacctac atctgcaacg tgaaccacaa accgagcaac   720
actaaagtgg ataaaaaagt tgaaccgaag tcttgctagt gatctagagt cgacctgcag   780
gtctatggaa cgataaatgc ccatgaaaat tctatttcaa ggagacagtc ataatgaaat   840
accttctgcc gaccgctgcc gctggt                                        866
```

<210> SEQ ID NO 6
<211> LENGTH: 247
<212> TYPE: PRT
<213> ORGANISM: Artificial Sequence
<220> FEATURE:
<223> OTHER INFORMATION: Amino acid of optimized VB6-845 heavy chain
      with RBS and leader

<400> SEQUENCE: 6

```
Met Lys Tyr Leu Leu Pro Thr Ala Ala Ala Gly Leu Leu Leu Leu Ala
 1               5                  10                  15

Ala Gln Pro Ala Met Ala His His His His His His Glu Val Gln Leu
            20                  25                  30

Val Gln Ser Gly Pro Gly Leu Val Gln Pro Gly Gly Ser Val Arg Ile
        35                  40                  45

Ser Cys Ala Ala Ser Gly Tyr Thr Phe Thr Asn Tyr Gly Met Asn Trp
    50                  55                  60

Val Lys Gln Ala Pro Gly Lys Gly Leu Glu Trp Met Gly Trp Ile Asn
65                  70                  75                  80

Thr Tyr Thr Gly Glu Ser Thr Tyr Ala Asp Ser Phe Lys Gly Arg Phe
                85                  90                  95

Thr Phe Ser Leu Asp Thr Ser Ala Ser Ala Ala Tyr Leu Gln Ile Asn
            100                 105                 110

Ser Leu Arg Ala Glu Asp Thr Ala Val Tyr Tyr Cys Ala Arg Phe Ala
        115                 120                 125

Ile Lys Gly Asp Tyr Trp Gly Gln Gly Thr Leu Leu Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190
```

Gly Val His Thr Phe Pro Ala Val Leu Gln Ser Ser Gly Leu Tyr Ser
            195                 200                 205

Leu Ser Ser Val Val Thr Val Pro Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys
                245

<210> SEQ ID NO 7
<211> LENGTH: 768
<212> TYPE: DNA
<213> ORGANISM: Artificial Sequence
<220> FEATURE:
<223> OTHER INFORMATION: Nucleotide sequence of optimized VB6-845 light
      chain with RBS and leader

<400> SEQUENCE: 7
aaggagaatt ccataatgaa atatctgctg ccgactgctg ctgcgggtct gctgctgctg      60
gctgcgcaac cggctatggc tcatcaccac caccaccatg acatccagat gacccagtcc     120
ccgtctagcc tgagcgcaag cgttggtgac cgtgtgacca tcacctgccg tagcactaaa    180
tccctgctgc actctaacgg catcacctac ctgtattggt accaacagaa accgggtaaa    240
gctccgaaac tgctgatcta ccagatgtct aacctggcta gcggcgttcc ttctcgtttt    300
tcttctagcg gtagcggtac tgacttcacc ctgaccatta gctctctgca gcctgaagac    360
tttgcgacct actattgcgc tcagaacctt gaaatcccgc gtaccttcgg ccagggtacc    420
aaagttgaac tgaagcgtac cgttgcggct ccgtctgttt tcatcttccc acctagcgat    480
gaacagctta atctggtac tgctagcgta gtttgcctgc ttaacaactt ctaccctcgt    540
gaagctaaag ttcagtggaa agttgacaac gctctgcagt ctggtaactc tcaggaatct    600
gtgaccgaac aggatagcaa agatagcacc tatagcctgt ctagcaccct gaccctt agc    660 aaggcggact atgaaaaaca caaagtttac gcttgcgagg tgacccacca aggtctgtct    720
tctccggtga ctaaatcctt taaccgtggc gaatgctagt gactcgag                  768

<210> SEQ ID NO 8
<211> LENGTH: 247
<212> TYPE: PRT
<213> ORGANISM: Artificial Sequence
<220> FEATURE:
<223> OTHER INFORMATION: Amino acid of optimized VB6-845 light chain
      with RBS and leader

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala His His His His His His Asp Ile Gln Met
            20                  25                  30

Thr Gln Ser Pro Ser Ser Leu Ser Ala Ser Val Gly Asp Arg Val Thr
        35                  40                  45

Ile Thr Cys Arg Ser Thr Lys Ser Leu Leu His Ser Asn Gly Ile Thr
    50                  55                  60

Tyr Leu Tyr Trp Tyr Gln Gln Lys Pro Gly Lys Ala Pro Lys Leu Leu
65                  70                  75                  80

Ile Tyr Gln Met Ser Asn Leu Ala Ser Gly Val Pro Ser Arg Phe Ser
                85                  90                  95

Ser Ser Gly Ser Gly Thr Asp Phe Thr Leu Thr Ile Ser Ser Leu Gln

Pro Glu Asp Phe Ala Thr Tyr Tyr Cys Ala Gln Asn Leu Glu Ile Pro
            115                 120                 125
Arg Thr Phe Gly Gln Gly Thr Lys Val Glu Leu Lys Arg Thr Val Ala
        130                 135                 140
Ala Pro Ser Val Phe Ile Phe Pro Pro Ser Asp Glu Gln Leu Lys Ser
145                 150                 155                 160
Gly Thr Ala Ser Val Val Cys Leu Leu Asn Asn Phe Tyr Pro Arg Glu
                165                 170                 175
Ala Lys Val Gln Trp Lys Val Asp Asn Ala Leu Gln Ser Gly Asn Ser
            180                 185                 190
Gln Glu Ser Val Thr Glu Gln Asp Ser Lys Asp Ser Thr Tyr Ser Leu
        195                 200                 205
Ser Ser Thr Leu Thr Leu Ser Lys Ala Asp Tyr Glu Lys His Lys Val
    210                 215                 220
Tyr Ala Cys Glu Val Thr His Gln Gly Leu Ser Ser Pro Val Thr Lys
225                 230                 235                 240
Ser Phe Asn Arg Gly Glu Cys
                245

<210> SEQ ID NO 9
<211> LENGTH: 861
<212> TYPE: DNA
<213> ORGANISM: Artificial Sequence
<220> FEATURE:
<223> OTHER INFORMATION: Nucleotide sequence of optimized bouganin with
      RBS and leader

<400> SEQUENCE: 9
aaggagaatt ccataatgaa atatctgctg ccgactgctg ctgcgggtct gctgctgctg      60
gctgcgcaac cggctatggc tcatcaccac caccaccatt ataacaccgt atcttttaac     120
ctgggtgagg cgtatgaata cccgaccttc atccaggacc tgcgtaatga acttgctaaa     180
ggtaccccct gtttgccagct gcctgtgacc ctgcagacca tcgctgatga taaacgtttc     240
gttctggttg acattaccac cacctccaaa aaaaccgtta agtcgcgat cgatgtgacc     300
gacgtttacg tggtaggtta ccaggataaa tgggacggta agatcgtgc ggttttcctg     360
gacaaagttc cgaccgtagc gacttctaaa ctgttcccag gtgtgaccaa ccgtgtgacc     420
ctgaccttcg acggcagcta tcagaaactg gttaacgcgg ccaaagctga tcgtaaagct     480
ctcgaactgg gtgttaacaa actggagttc agcattgaag ctatccacgg taaaaccatc     540
aacggtcaag aagcagctaa attcttcctg atcgtgatcc agatggttag cgaagcagcg     600
cgttttaaat acattgaaac cgaagtagtt gatcgtggtc tgtatggtag cttcaaaccg     660
aacttcaaag ttcttaacct ggagaacaac tggggtgaca ttagcgacgc gatccataaa     720
tcttccccgc aatgcaccac cattaacccg gctctgcagc tgatctctcc gtctaacgat     780
ccgtgggtag ttaacaaagt gtctcaaatc agcccggaca tgggtatcct gaaatttaaa     840
tctagcaaat agtgactcga g                                                861

<210> SEQ ID NO 10
<211> LENGTH: 278
<212> TYPE: PRT
<213> ORGANISM: Artificial Sequence
<220> FEATURE:
<223> OTHER INFORMATION: Amino acid sequence of optimized bouganin with
      RBS and leader

<400> SEQUENCE: 10

```
Met Lys Tyr Leu Leu Pro Thr Ala Ala Gly Leu Leu Leu Leu Ala
1               5                   10                  15
Ala Gln Pro Ala Met Ala His His His His His Tyr Asn Thr Val
            20                  25                  30
Ser Phe Asn Leu Gly Glu Ala Tyr Glu Tyr Pro Thr Phe Ile Gln Asp
        35                  40                  45
Leu Arg Asn Glu Leu Ala Lys Gly Thr Pro Val Cys Gln Leu Pro Val
    50                  55                  60
Thr Leu Gln Thr Ile Ala Asp Asp Lys Arg Phe Val Leu Val Asp Ile
65                  70                  75                  80
Thr Thr Thr Ser Lys Lys Thr Val Lys Val Ala Ile Asp Val Thr Asp
                85                  90                  95
Val Tyr Val Val Gly Tyr Gln Asp Lys Trp Asp Gly Lys Asp Arg Ala
            100                 105                 110
Val Phe Leu Asp Lys Val Pro Thr Val Ala Thr Ser Lys Leu Phe Pro
        115                 120                 125
Gly Val Thr Asn Arg Val Thr Leu Thr Phe Asp Gly Ser Tyr Gln Lys
    130                 135                 140
Leu Val Asn Ala Ala Lys Ala Asp Arg Lys Ala Leu Glu Leu Gly Val
145                 150                 155                 160
Asn Lys Leu Glu Phe Ser Ile Glu Ala Ile His Gly Lys Thr Ile Asn
                165                 170                 175
Gly Gln Glu Ala Ala Lys Phe Phe Leu Ile Val Ile Gln Met Val Ser
            180                 185                 190
Glu Ala Ala Arg Phe Lys Tyr Ile Glu Thr Glu Val Val Asp Arg Gly
        195                 200                 205
Leu Tyr Gly Ser Phe Lys Pro Asn Phe Lys Val Leu Asn Leu Glu Asn
    210                 215                 220
Asn Trp Gly Asp Ile Ser Asp Ala Ile His Lys Ser Ser Pro Gln Cys
225                 230                 235                 240
Thr Thr Ile Asn Pro Ala Leu Gln Leu Ile Ser Pro Ser Asn Asp Pro
                245                 250                 255
Trp Val Val Asn Lys Val Ser Gln Ile Ser Pro Asp Met Gly Ile Leu
            260                 265                 270
Lys Phe Lys Ser Ser Lys
        275

<210> SEQ ID NO 11
<211> LENGTH: 348
<212> TYPE: DNA
<213> ORGANISM: Artificial Sequence
<220> FEATURE:
<223> OTHER INFORMATION: Optimized nucleotide sequence of VB6-845 heavy
      chain VH

<400> SEQUENCE: 11
gaggttcagc tggtccagtc cggtccgggt ctggttcagc cgggtggtag cgttcgtatt     60
agctgcgcgg cgagcggtta caccttcacc aactacggta tgaactgggt taaacaggct    120
ccgggtaaag gtttggaatg gatgggttgg atcaacacct ataccggtga gtctacctac    180
gctgatagct tcaaaggccg tttcaccttt agccttgaca cttctgcgag cgcggcgtac    240
ctgcagatta actctctgcg tgctgaggac actgcggttt actactgcgc tcgtttcgcg    300
atcaaaggtg actattgggg tcagggtact ctgctgaccg ttagcagc                348

<210> SEQ ID NO 12
```

<211> LENGTH: 348
<212> TYPE: DNA
<213> ORGANISM: Artificial Sequence
<220> FEATURE:
<223> OTHER INFORMATION: Nucleotide sequence of VB6-845 heavy chain VH

<400> SEQUENCE: 12

```
gaagtacagc tggttcagtc cggcccgggt cttgttcaac cgggtggttc cgttcgtatc    60
tcttgcgctg cttctggtta cacgttcacc aactacggca tgaactgggt caaacaggct   120
ccgggtaaag gcctggaatg gatgggctgg atcaacacct acaccggtga atccacctac   180
gctgactcct tcaaaggtcg cttcactttc tccctcgaca aagtgctag tgctgcatac    240
ctccaaatca actcgctgcg tgcagaggat acagcagtct attactgcgc cgtttcgct    300
atcaaaggtg actactgggg tcaaggcacg ctgctgaccg tttcctcg               348
```

<210> SEQ ID NO 13
<211> LENGTH: 315
<212> TYPE: DNA
<213> ORGANISM: Artificial Sequence
<220> FEATURE:
<223> OTHER INFORMATION: Optimized nucleotide sequence of VB6-845 heavy
      chain CH

<400> SEQUENCE: 13

```
gctagcacta aaggtccgtc cgttttccca ctggctccgt cttctaaaag cacttctggt    60
ggtaccgcgg ctctgggttg ccttgttaaa gactacttcc ctgaaccggt caccgttagc   120
tggaactccg gtgcgttgac ctctggtgtt cacaccttcc cagcggttct gcagtctagc   180
ggtctgtata gcctgagctc tgtagttacc gttccgtctt ctagcctggg tacgcagacc   240
tacatctgca acgtgaacca caaaccgagc aacactaaag tggataaaaa agttgaaccg   300
aagtcttgct agtga                                                   315
```

<210> SEQ ID NO 14
<211> LENGTH: 315
<212> TYPE: DNA
<213> ORGANISM: Artificial Sequence
<220> FEATURE:
<223> OTHER INFORMATION: Nucleotide sequence of VB6-845 heavy chain CH

<400> SEQUENCE: 14

```
gctagcacca aaggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca ccgtgaatca caagcccagc aacaccaagg tggacaagaa agttgagccc   300
aaatcttgtt agtga                                                   315
```

<210> SEQ ID NO 15
<211> LENGTH: 339
<212> TYPE: DNA
<213> ORGANISM: Artificial Sequence
<220> FEATURE:
<223> OTHER INFORMATION: Optimized nucleotide sequence of VB6-845 heavy
      chain VL

<400> SEQUENCE: 15

```
gacatccaga tgacccagtc cccgtctagc ctgagcgcaa gcgttggtga ccgtgtgacc    60
atcacctgcc gtagcactaa atccctgctg cactctaacg gcatcaccta cctgtattgg   120
```

-continued

| | |
|---|---|
| taccaacaga aaccgggtaa agctccgaaa ctgctgatct accagatgtc taacctggct | 180 |
| agcggcgttc cttctcgttt ttcttctagc ggtagcggta ctgacttcac cctgaccatt | 240 |
| agctctctgc agcctgaaga ctttgcgacc tactattgcg ctcagaacct tgaaatcccg | 300 |
| cgtaccttcg gccagggtac caaagttgaa ctgaagcgt | 339 |

<210> SEQ ID NO 16
<211> LENGTH: 339
<212> TYPE: DNA
<213> ORGANISM: Artificial Sequence
<220> FEATURE:
<223> OTHER INFORMATION: Nucleotide sequence of VB6-845 heavy chain VL

<400> SEQUENCE: 16

| | |
|---|---|
| gatatccaga tgacccagtc cccgtcctcc ctgagtgctt ctgttggtga ccgtgttacc | 60 |
| atcacctgcc gttccaccaa atccctcctg cactccaacg gtatcaccta cctttattgg | 120 |
| tatcaacaga aacgggtaa agctccgaaa cttctgatct accagatgtc caacctggct | 180 |
| tccggtgttc cgtctcgttt ctccagttct ggttctggta ccgacttcac cctgaccatc | 240 |
| tcttctctgc agccggaaga cttcgctacc tactactgcg ctcagaacct ggaaatcccg | 300 |
| cgtaccttcg gtcagggtac caaagttgaa cttaagcgc | 339 |

<210> SEQ ID NO 17
<211> LENGTH: 318
<212> TYPE: DNA
<213> ORGANISM: Artificial Sequence
<220> FEATURE:
<223> OTHER INFORMATION: Optimized nucleotide sequence of VB6-845 heavy
      chain CL

<400> SEQUENCE: 17

| | |
|---|---|
| accgttgcgg ctccgtctgt tttcatcttc ccacctagcg atgaacagct taaatctggt | 60 |
| actgctagcg tagtttgcct gcttaacaac ttctaccctc gtgaagctaa agttcagtgg | 120 |
| aaagttgaca acgctctgca gtctggtaac tctcaggaat ctgtgaccga acaggatagc | 180 |
| aaagatagca cctatagcct gtctagcacc ctgaccctta gcaaggcgga ctatgaaaaa | 240 |
| cacaaagttt acgcttgcga ggtgacccac caaggtctgt cttctccggt gactaaatcc | 300 |
| tttaaccgtg gcgaatgc | 318 |

<210> SEQ ID NO 18
<211> LENGTH: 318
<212> TYPE: DNA
<213> ORGANISM: Artificial Sequence
<220> FEATURE:
<223> OTHER INFORMATION: Nucleotide sequence of VB6-845 heavy chain CL

<400> SEQUENCE: 18

| | |
|---|---|
| actgtggctg caccatctgt cttcatcttc ccgccatctg atgagcagtt gaaatctgga | 60 |
| actgcctctg ttgtgtgcct gctgaataac ttctatccca gagaggccaa agtacagtgg | 120 |
| aaggtggata acgccctcca atcgggtaac tcccaggaga gtgtcacaga gcaggacagc | 180 |
| aaggacagca cctacagcct cagcagcacc ctgacgctga gcaaagcaga ctacgagaaa | 240 |
| cacaaagtct acgcctgcga agtcacccat cagggcctga gctcgcccgt cacaaagagc | 300 |
| ttcaacaggg gagagtgt | 318 |

<210> SEQ ID NO 19
<211> LENGTH: 750
<212> TYPE: DNA
<213> ORGANISM: Artificial Sequence
<220> FEATURE:
<223> OTHER INFORMATION: Optimized nucleotide sequence of bouganin

<400> SEQUENCE: 19

| | | | | | |
|---|---|---|---|---|---|
| tataacaccg | tatcttttaa | cctgggtgag | gcgtatgaat | acccgacctt | catccaggac | 60 |
| ctgcgtaatg | aacttgctaa | aggtacccct | gtttgccagc | tgcctgtgac | cctgcagacc | 120 |
| atcgctgatg | ataaacgttt | cgttctggtt | gacattacca | ccacctccaa | aaaaaccgtt | 180 |
| aaagtcgcga | tcgatgtgac | cgacgtttac | gtggtaggtt | accaggataa | atgggacggt | 240 |
| aaagatcgtg | cggttttcct | ggacaaagtt | ccgaccgtag | cgacttctaa | actgttccca | 300 |
| ggtgtgacca | accgtgtgac | cctgaccttc | gacggcagct | atcagaaact | ggttaacgcg | 360 |
| gccaaagctg | atcgtaaagc | tctcgaactg | gtgttaaca | aactggagtt | cagcattgaa | 420 |
| gctatccacg | taaaaccat | caacggtcaa | gaagcagcta | aattcttcct | gatcgtgatc | 480 |
| cagatggtta | gcgaagcagc | gcgttttaaa | tacattgaaa | ccgaagtagt | tgatcgtggt | 540 |
| ctgtatggta | gcttcaaacc | gaacttcaaa | gttcttaacc | tggagaacaa | ctggggtgac | 600 |
| attagcgacg | cgatccataa | atcttccccg | caatgcacca | ccattaaccc | ggctctgcag | 660 |
| ctgatctctc | cgtctaacga | tccgtgggta | gttaacaaag | tgtctcaaat | cagcccggac | 720 |
| atgggtatcc | tgaaatttaa | atctagcaaa | | | | 750 |

<210> SEQ ID NO 20
<211> LENGTH: 750
<212> TYPE: DNA
<213> ORGANISM: Artificial Sequence
<220> FEATURE:
<223> OTHER INFORMATION: Nucleotide sequence of bouganin

<400> SEQUENCE: 20

| | | | | | |
|---|---|---|---|---|---|
| tacaacaccg | tgtcatttaa | ccttggagaa | gcttatgagt | accccacttt | tatacaagat | 60 |
| ttgcgcaatg | aattggctaa | gggcacacca | gtatgtcaac | ttccagtgac | actacaaacc | 120 |
| atagccgatg | acaagcgatt | tgttctagtt | gatatcacta | cgacctcgaa | gaaaacagtt | 180 |
| aaggttgcta | tagatgtgac | agatgtgtat | gttgtgggtt | atcaagacaa | atgggatggc | 240 |
| aaagatcgag | ctgttttcct | tgacaaggtt | cctactgttg | caactagtaa | acttttccca | 300 |
| ggggtgacta | atcgtgtaac | gttaacattt | gatggcagct | atcagaaact | tgtgaatgct | 360 |
| gccaaagctg | atagaaaggc | tctcgaactg | ggggttaaca | aattggaatt | ttccattgaa | 420 |
| gcaatccatg | gtaaaacgat | aaatggtcaa | gaggcagcca | agttcttcct | tattgtcatc | 480 |
| caaatggttt | cagaggcagc | tcggttcaaa | tatattgaga | ctgaggtggt | tgatagagga | 540 |
| ttatatggat | cattcaaacc | taattttaaa | gtattgaact | tggagaacaa | ttggggcgac | 600 |
| atctctgatg | ccattcacaa | atcatcccca | caatgtacca | ctattaatcc | ggcacttcag | 660 |
| ttgataagcc | cctcaaatga | cccatgggtt | gtaaataaag | tgagtcaaat | tagtcccgat | 720 |
| atgggtatcc | ttaagtttaa | aagctccaaa | | | | 750 |

<210> SEQ ID NO 21
<211> LENGTH: 94
<212> TYPE: DNA
<213> ORGANISM: Artificial Sequence
<220> FEATURE:
<223> OTHER INFORMATION: First PelB and Initial Sequence including Histidines Optimized

<400> SEQUENCE: 21

| | | | | | |
|---|---|---|---|---|---|
| gaattccata | atgaaatatc | tgctgccgac | tgctgctgcg | ggtctgctgc | tgctggctgc | 60 |

```
gcaaccggct atggctcatc accaccacca ccat                              94
```

<210> SEQ ID NO 22
<211> LENGTH: 149
<212> TYPE: DNA
<213> ORGANISM: Artificial Sequence
<220> FEATURE:
<223> OTHER INFORMATION: First PelB and Initial Sequence including
      Histidines

<400> SEQUENCE: 22

```
gaattcctgc aggtctatgg aacgataaat gcccatgaaa attctatttc aaggagacag    60
tcataatgaa atacctattg cctacggcag ccgctggatt gttattactc gctgcccaac   120
cagcgatggc gcaccatcat caccatcac                                     149
```

<210> SEQ ID NO 23
<211> LENGTH: 137
<212> TYPE: DNA
<213> ORGANISM: Artificial Sequence
<220> FEATURE:
<223> OTHER INFORMATION: Second Pel B leader and Intervening Sequence
      optimized

<400> SEQUENCE: 23

```
tctagagtcg acctgcaggt ctatggaacg ataaatgccc atgaaaattc tatttcaagg    60
agacagtcat aatgaaatac cttctgccga ccgctgccgc tggtctgctg ctgttggctg   120
ctcaaccggc tatggca                                                  137
```

<210> SEQ ID NO 24
<211> LENGTH: 137
<212> TYPE: DNA
<213> ORGANISM: Artificial Sequence
<220> FEATURE:
<223> OTHER INFORMATION: Second Pel B leader and Intervening Sequence

<400> SEQUENCE: 24

```
tctagagtcg acctgcaggt ctatggaacg ataaatgccc atgaaaattc tatttcaagg    60
agacagtcat aatgaaatac ctattgccta cggcagccgc tggattgtta ttactcgctg   120
cccaaccagc gatggcg                                                  137
```

<210> SEQ ID NO 25
<211> LENGTH: 36
<212> TYPE: DNA
<213> ORGANISM: Artificial Sequence
<220> FEATURE:
<223> OTHER INFORMATION: Furin linker optimized

<400> SEQUENCE: 25

```
acccgtcacc gtcagccgcg tggttgggaa cagctg                              36
```

<210> SEQ ID NO 26
<211> LENGTH: 36
<212> TYPE: DNA
<213> ORGANISM: Artificial Sequence
<220> FEATURE:
<223> OTHER INFORMATION: Furin linker

<400> SEQUENCE: 26

```
accaggcaca ggcagcccag aggctgggag cagctc                              36
```